United States Patent
Huh et al.

(10) Patent No.: US 8,946,695 B2
(45) Date of Patent: Feb. 3, 2015

(54) COMPOUND, AND ORGANIC LIGHT-EMITTING DEVICE USING SAME

(75) Inventors: Jungoh Huh, Seoul (KR); Sung Kil Hong, Daejeon (KR); Yun Hwan Kim, Seoul (KR); Tae Yoon Park, Daejeon (KR); Hye Young Jang, Daejeon (KR); Kongkyeom Kim, Daejeon (KR); Seong So Kim, Gyeonggi-do (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 13/994,548

(22) PCT Filed: Dec. 27, 2011

(86) PCT No.: PCT/KR2011/010183
§ 371 (c)(1),
(2), (4) Date: Jun. 14, 2013

(87) PCT Pub. No.: WO2012/091428
PCT Pub. Date: Jul. 5, 2012

(65) Prior Publication Data
US 2013/0256649 A1  Oct. 3, 2013

(30) Foreign Application Priority Data
Dec. 29, 2010  (KR) .......................... 10-2010-0138130

(51) Int. Cl.
*H01L 29/08* (2006.01)
*H01L 51/00* (2006.01)
*C09K 11/06* (2006.01)
*C07C 211/54* (2006.01)
(Continued)

(52) U.S. Cl.
CPC ............ *H01L 51/0072* (2013.01); *C09K 11/06* (2013.01); *H01L 51/006* (2013.01); *C07C 211/54* (2013.01); *C07C 211/58* (2013.01); *C07C 211/61* (2013.01); *C07D 333/76* (2013.01); *C09K 2211/1007* (2013.01); *C09K 2211/1011* (2013.01); *C09K 2211/1014* (2013.01); *C09K 2211/1092* (2013.01); *H01L 51/0054* (2013.01); *H01L 51/0059* (2013.01); *C07C 2103/18* (2013.01); *C07C 2103/42* (2013.01)
USPC .............................. 257/40; 428/690; 428/696

(58) Field of Classification Search
None
See application file for complete search history.

(56) References Cited

U.S. PATENT DOCUMENTS

| 6,747,287 B1 | 6/2004 | Toguchi et al. | |
| 2002/0064679 A1* | 5/2002 | Ishiskawa et al. | 428/690 |
| 2010/0001636 A1 | 1/2010 | Yabunouchi | |

FOREIGN PATENT DOCUMENTS

| DE | 650058 C | 9/1937 |
| JP | 11-251063 A | 9/1999 |

(Continued)

OTHER PUBLICATIONS

Bavin P.M.G., et al.: "Electrophilic Substitution. Part I. Preliminary Investigations", Journal of the Chemical Society, Jan. 1, 1956, pp. 164-169, XP-002727421.

*Primary Examiner* — Kyoung Lee
(74) *Attorney, Agent, or Firm* — McKenna Long & Aldridge LLP

(57) ABSTRACT

The present invention provides a new compound which may significantly improve the service life, efficiency, electrochemical stability, and thermal stability of an organic light emitting device, and an organic light emitting device which comprises an organic material layer comprising the compound.

12 Claims, 1 Drawing Sheet

(51) Int. Cl.
*C07C 211/58* (2006.01)
*C07C 211/61* (2006.01)
*C07D 333/76* (2006.01)

(56) References Cited

FOREIGN PATENT DOCUMENTS

| | | |
|---|---|---|
| JP | 11-255781 A | 9/1999 |
| JP | 1999-251063 A | 9/1999 |
| JP | 2003-124472 A | 4/2003 |
| JP | 2005-71983 A | 3/2005 |
| JP | 2005-071983 A | 3/2005 |
| JP | 2005-259472 A | 9/2005 |
| JP | 2009-292760 A | 12/2009 |
| JP | 2011-118172 A | 6/2011 |
| KR | 10-0753454 B1 | 8/2007 |
| WO | 2009/145016 A1 | 12/2009 |
| WO | 2010/002850 A1 | 1/2010 |
| WO | WO 2010-002850 A1 | 1/2010 |
| WO | 2010/050779 A1 | 5/2010 |
| WO | 2011/133007 A9 | 10/2011 |
| WO | 2011/139129 A2 | 11/2011 |

\* cited by examiner

COMPOUND, AND ORGANIC LIGHT-EMITTING DEVICE USING SAME

This Application is a 35 U.S.C. §371 National Stage Entry of International Application No. PCT/KR2011/010183, filed on Dec. 27, 2011, which claims priority to Korean Patent application No. 10-2010-0138130, filed on Dec. 29, 2010, both of which are incorporated by reference in their entirety herein.

TECHNICAL FIELD

This application claims priority to and the benefit of Korean Patent Application No. 10-2010-0138130 filed in the Korean Intellectual Property Office on Dec. 29, 2010, the entire contents of which are incorporated herein by reference.

The present invention relates to an organic light emitting device containing a novel compound, which may significantly improve the service life, efficiency, electrochemical stability, and thermal stability of the organic light emitting device, in an organic compound layer.

BACKGROUND ART

An organic light emission phenomenon is an example of converting current into visible rays through an internal process of a specific organic molecule. The principle of the organic light emission phenomenon is based on the following mechanism. When an organic material layer is disposed between a positive electrode and a negative electrode, if voltage is applied between the two electrodes, electrons and holes are injected from the negative electrode and the positive electrode, respectively, into the organic material layer. The electrons and the holes which are injected into the organic material layer are recombined to form an exciton, and the exciton is reduced to a bottom state to emit light. An organic light emitting device using this principle may typically comprise a negative electrode, a positive electrode, and an organic material layer, for example, an organic material layer comprising a hole injection layer, a hole transporting layer, a light emitting layer, and an electron transporting layer, disposed therebetween.

The materials used in the organic light emitting device are mostly pure organic materials or complexes of organic materials with metals, and may be classified as a hole injection material, a hole transporting material, a light emitting material, an electron transporting material, or an electron injection material, according to their use. In connection with this, an organic material having a p-type property, which is easily oxidized and electrochemically stable when it is oxidized, is usually used as the hole injection material or the hole transporting material. Meanwhile, an organic material having an n-type property, which is easily reduced and is electrochemically stable when it is reduced, is usually used as the electron injection material or the electron transporting material. As the light emitting layer material, a material having both p-type and n-type properties is preferable, which is stable when it is oxidized and when it is reduced. When an exciton is formed, a material having high light emitting efficiency for converting the exciton into light is preferable.

In addition, it is preferred that the material used in the organic light emitting device further has the following properties.

First, it is preferred that the material used in the organic light emitting device has excellent thermal stability. This is due to joule heat generated by movement of the electric charges in the organic light emitting device. NPB, which has currently been used as the hole transporting layer material, has a glass transition temperature of 100° C. or less, and thus it is difficult to apply NPB to an organic light emitting device requiring a high current.

Second, in order to obtain an organic light emitting device that is capable of being driven at low voltage and has high efficiency, holes or electrons which are injected into the organic light emitting device need to be smoothly transported to a light emitting layer, and simultaneously the injected holes and electrons need to be prevented from being released out of the light emitting layer. To achieve this, a material used in the organic light emitting device needs to have a proper band gap and proper HOMO and LUMO energy levels. A LUMO energy level of PEDOT:PSS, which is currently used as a hole transporting material of an organic light emitting device manufactured by using a solution coating method, is lower than that of an organic material used as a light emitting layer material, and thus it is difficult to manufacture an organic light emitting device having high efficiency and a long service life.

Moreover, the material used in the organic light emitting device needs to have excellent chemical stability, electric charge mobility, and interfacial characteristic with an electrode or an adjacent layer. That is, the material used in the organic light emitting device needs to be minimally deformed by moisture or oxygen. Furthermore, a proper hole or electron mobility needs to be assured so as to balance densities of the holes and of the electrons in the light emitting layer of the organic light emitting device to maximize the formation of excitons. Additionally, it needs to be able to have a good interface with an electrode comprising metal or metal oxides so as to assure stability of the device.

Accordingly, there is a need to develop an organic material having the above-described requirements in the art.

DETAILED DESCRIPTION OF THE INVENTION

Technical Problem

The present invention has been made in an effort to provide an organic light emitting device comprising a compound which satisfies conditions required for materials available in the organic light emitting device, for example, proper energy level, electrochemical stability, thermal stability, and the like, and has a chemical structure capable of serving various roles required for the organic light emitting device depending on the substituent group.

Technical Solution

An exemplary embodiment of the present invention provides a compound represented by the following Formula 1.

[Formula 1]

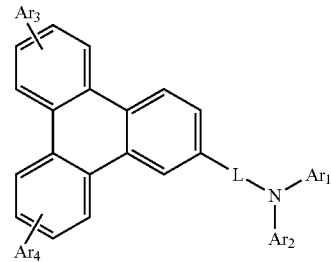

Wherein $Ar_1$ and $Ar_2$ are the same as or different from each other and are each independently selected from the group consisting of hydrogen; deuterium; an alkyl group that is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxy group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a hetero ring group comprising O, N or S as a heteroatom, which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a carbazolyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a fluorenyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; an aryloxy group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; an arylthio group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; and an alkoxycarbonyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group, L is a direct bond; an arylene group having 6 to 40 carbon atoms, which is unsubstituted or substituted by one or more substituent groups selected from the group consisting of nitro, nitrile, halogen, an alkyl group, and an alkoxy group; a divalent hetero ring group which is unsubstituted or substituted by one or more substituent groups selected from the group consisting of nitro, nitrile, halogen, an alkyl group, and an alkoxy group; or a fluorenylene group which is unsubstituted or substituted by one or more substituent groups selected from the group consisting of nitro, nitrile, halogen, an alkyl group, and an alkoxy group, except that L is a direct bond and both of $Ar_1$ and $Ar_2$ are a phenyl group having 6 carbon atoms or a tolyl group having 7 carbon atoms, $Ar_3$ and $Ar_4$ are the same as or different from each other and are each independently selected from the group consisting of hydrogen; deuterium; tritium; an alkenyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; an aryl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a hetero ring group comprising O, N or S as a heteroatom, which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a carbazolyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a fluorenyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; and nitrile group.

In addition, the present invention provides an organic light emitting device, comprising: a first electrode; a second electrode: and an organic material layer having one or more layers disposed between the first electrode and the second electrode, wherein one or more layers of the organic material layer comprise a compound represented by the following Formula 1.

Advantageous Effects

A compound of the present invention may be used as an organic material layer material, particularly, a hole injection material and/or a hole transporting material in an organic light emitting device, and when the compound is used in the organic light emitting device, a driving voltage of the device may be reduced, light efficiency may be improved, and a life span property of the device may be improved by thermal stability of the compound.

BEST MODE

Figure 1:
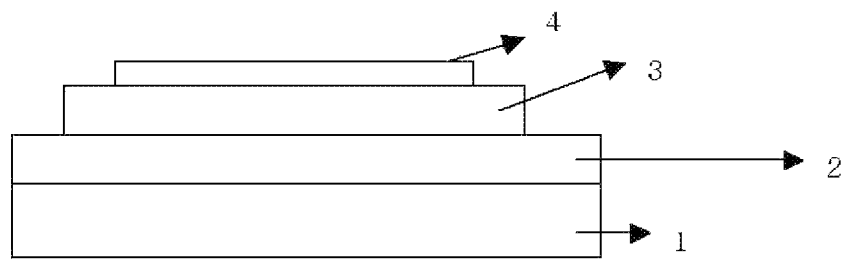
FIG. 1 illustrates an example of an organic light emitting device comprising a substrate 1, a positive electrode 2, a light emitting layer 3, and a negative electrode 4.

Hereinafter, the present invention will be described in detail.

A new compound according to the present invention is represented by the following Formula 1.

In the compound according to the present invention, the substituent groups in Formula 1 will be described in more detail as follows.

Examples of the halogen group comprise fluorine, chlorine, bromine, iodine, and the like, but are not limited thereto.

The alkyl group may be straight or branched, and the number of carbon atoms is not particularly limited, but is preferably 1 to 12. Specific examples thereof comprise a methyl group, an ethyl group, a propyl group, an isopropyl group, a butyl group, a t-butyl group, a pentyl group, a hexyl group, a heptyl group, and the like, but are not limited thereto.

The alkenyl group may be straight or branched, and the number of carbon atoms is not particularly limited, but is preferably 2 to 12. Specific examples thereof comprise an alkenyl group which is connected to an aryl group such as a stylbenzyl group, a styrenyl group, and the like, but are not limited thereto.

The cycloalkyl group preferably has 3 to 12 carbon atoms, and does not cause a steric hindrance. Specific examples thereof comprise a cyclopentyl group, a cyclohexyl group, and the like, but are not limited thereto.

The alkoxy group preferably has 1 to 12 carbon atoms, and more specifically, examples thereof comprise a methoxy group, an ethoxy group, an isopropyl oxy group, and the like, but are not limited thereto.

The aryl group may be monocyclic or polycyclic, and the number of carbon atoms is not particularly limited, but is preferably 6 to 40. Examples of the monocyclic aryl group comprise a phenyl group, a biphenyl group, a terphenyl group, a stilbene group, and the like, examples of the polycyclic aryl group comprise a naphthyl group, an anthracenyl group, a phenanthrene group, a pyrenyl group, a perylenyl group, a chrysenyl group, and the like, but are not limited thereto.

The heteroaryl group is a ring group comprising O, N, S, or P as a hetero atom, and the number of carbon atoms is not particularly limited, but is preferably 3 to 30. Examples of the hetero ring group comprise a carbazole group, a thiophene group, a furan group, a pyrrole group, an imidazole group, a thiazole group, an oxazole group, an oxadiazole group, a triazole group, a pyridyl group, a pyradazine group, a quinolinyl group, an isoquinoline group, an acridyl group, and the like, and compounds having the following structural formulas are preferable, but are not limited thereto.

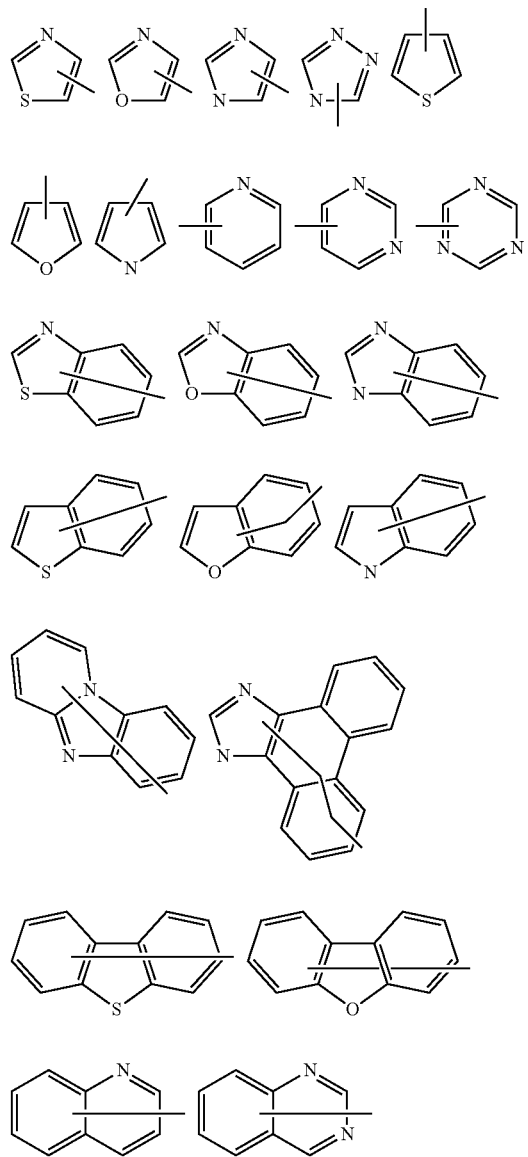

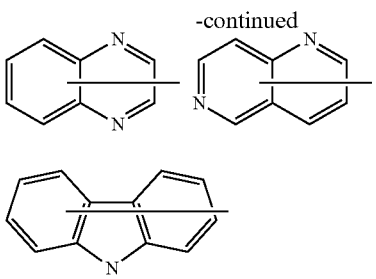

Further, as used herein, the term "substituted or unsubstituted" means that a group is substituted by one or more substituent groups selected from the group consisting of deuterium, a halogen group, an alkyl group, an alkenyl group, an alkoxy group, a silyl group, an arylalkenyl group, an aryl group, a heteroaryl group, a carbazole group, a fluorenyl group which is unsubstituted or substituted by an aryl group, and a nitrile group, or does not have any substituent group.

Examples of the substituent groups which may be additionally substituted in $Ar_1$ to $Ar_4$ and L in Formula 1 comprise a halogen group, an alkyl group, an alkenyl group, an alkoxy group, a silyl group, an arylalkenyl group, an aryl group, a heteroaryl group, a carbazole group, a fluorenyl group which is unsubstituted or substituted by an aryl group, a nitrile group, and the like, but are not limited thereto.

It is preferable that $Ar_1$ and $Ar_2$ in Formula 1 are the same as or different from each other and are each independently selected from the group consisting of an aryl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a hetero ring group comprising O, N or S as a heteroatom, which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a carbazolyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; and a fluorenyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group.

L in Formula 1 is preferably a direct bond; or an arylene group having 6 to 40 carbon atoms, which is unsubstituted or substituted by one or more substituent groups selected from the group consisting of nitro, nitrile, halogen, an alkyl group, and an alkoxy group. However, the case where L is a direct bond and both of $Ar_1$ and $Ar_2$ are a phenyl group having 6 carbon atoms or a tolyl group having 7 carbon atoms is excluded.

It is preferable that $Ar_3$ and $Ar_4$ in Formula 1 are the same as or different from each other and are each independently selected from the group consisting of hydrogen; deuterium; an aryl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; and a hetero ring group comprising O, N or S as a heteroatom, which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group.

Formula 1 may be represented by the following Formula 2 or 3, but is not limited thereto.

[Formula 2]

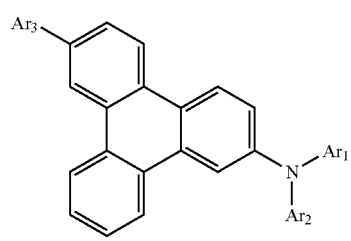

[Formula 3]

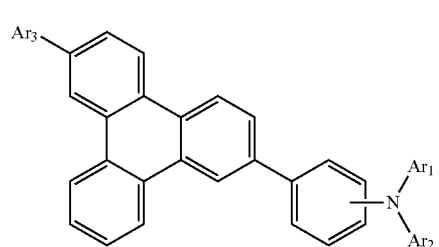

Wherein $Ar_1$ to $Ar_3$ are the same as those defined in Formula 1.

The compound according to the present invention may be more specifically exemplified by the following compounds, but the present invention is not limited thereto.

[Formula 1-1]
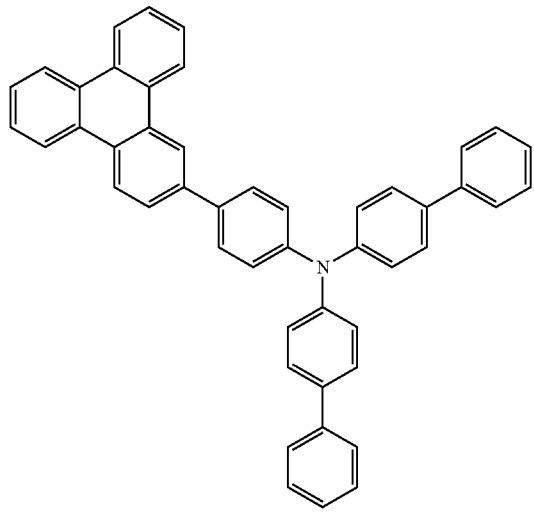
[Formula 1-2]
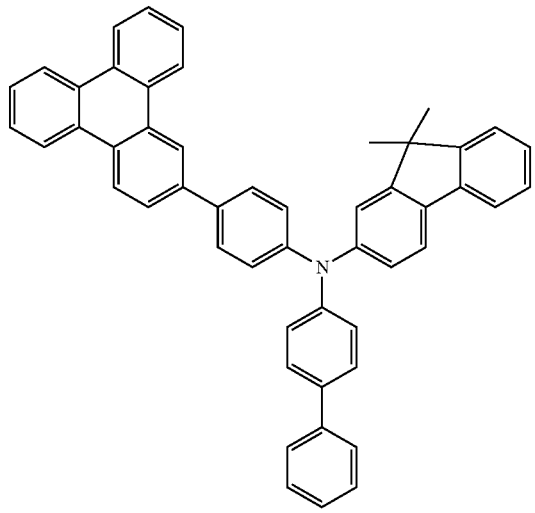
[Formula 1-3]
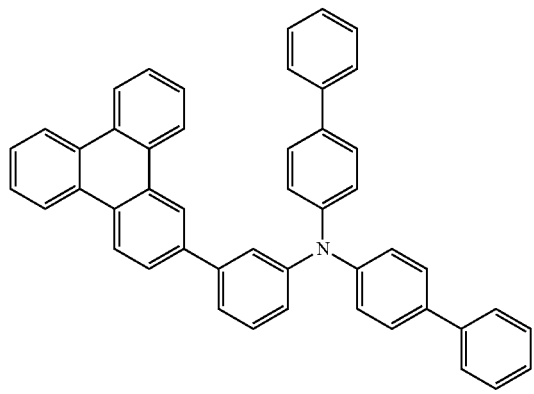
[Formula 1-4]
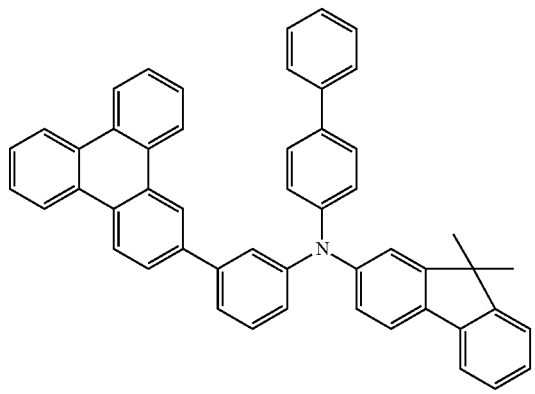
[Formula 1-5]
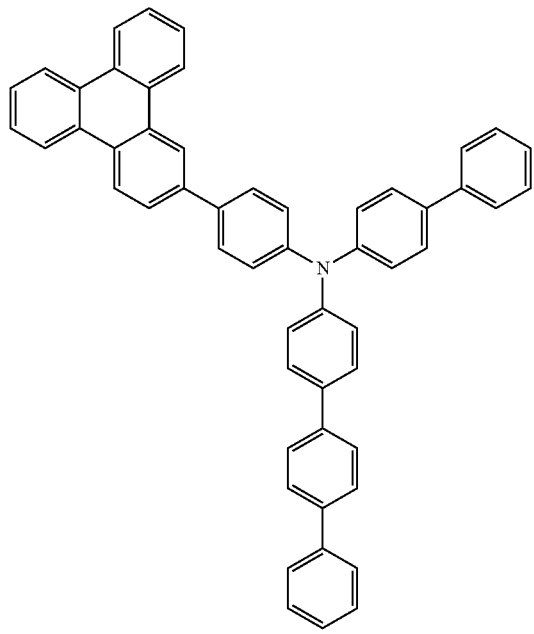
[Formula 1-6]
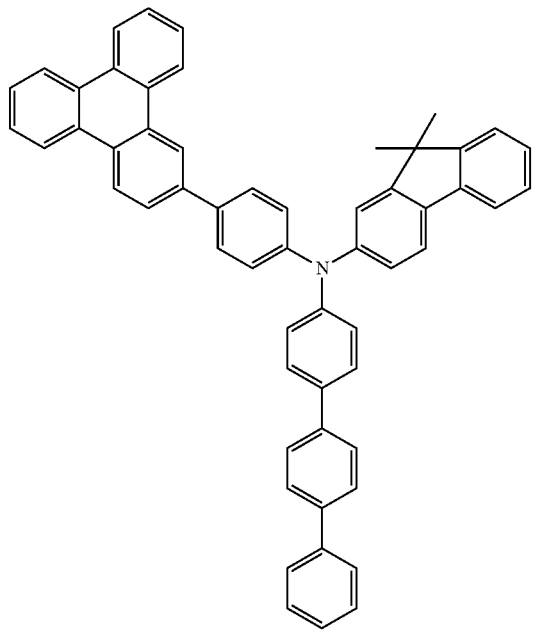

[Formula 1-7]
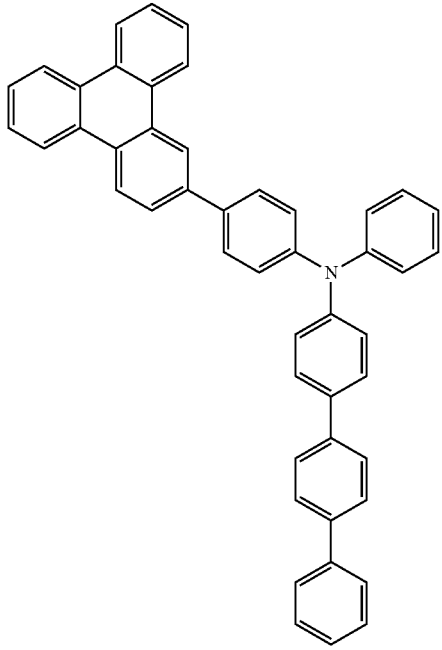
[Formula 1-8]
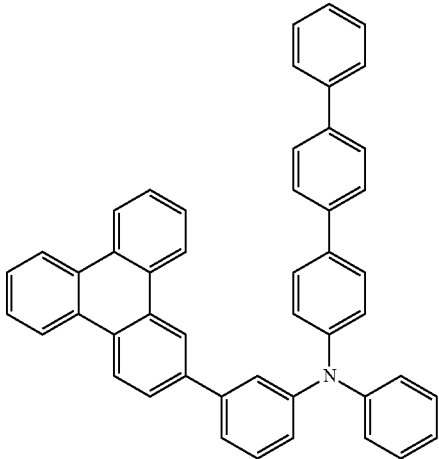
[Formula 1-9]
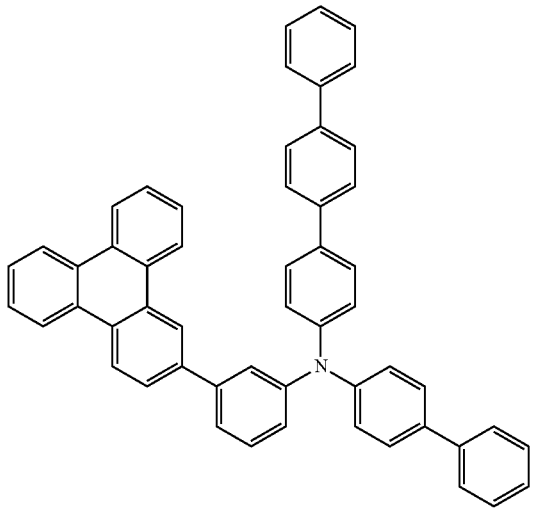
[Formula 1-10]
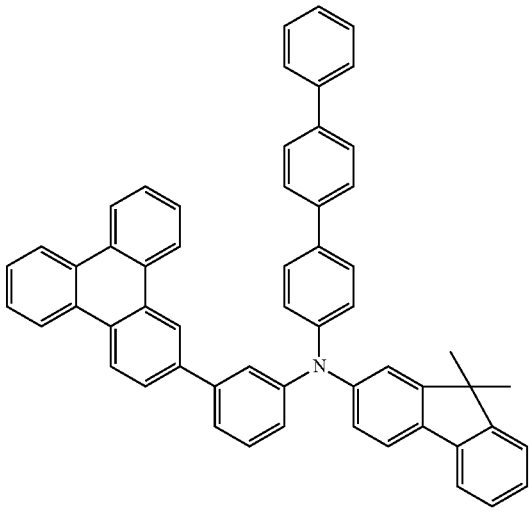
[Formula 1-11]
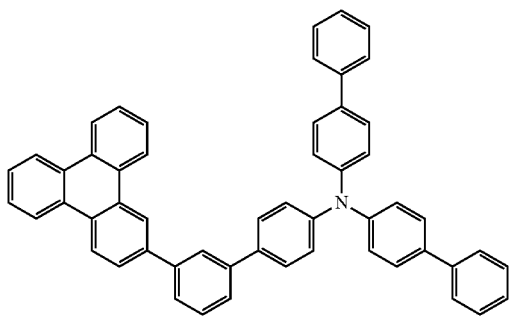
[Formula 1-12]
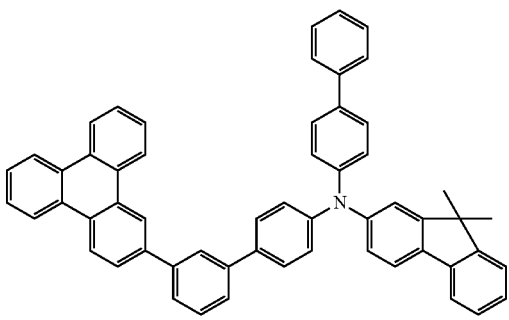

-continued
[Formula 1-13]
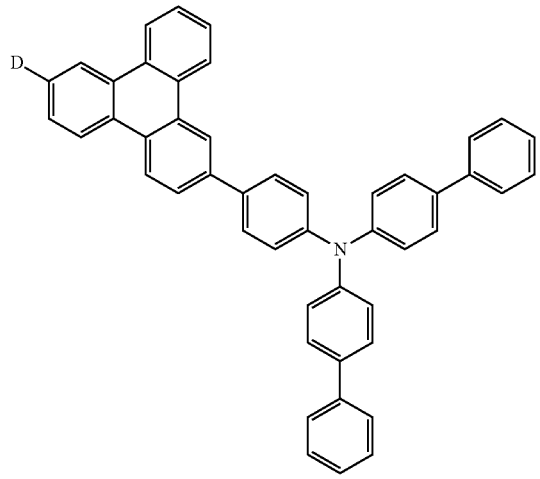
[Formula 1-14]
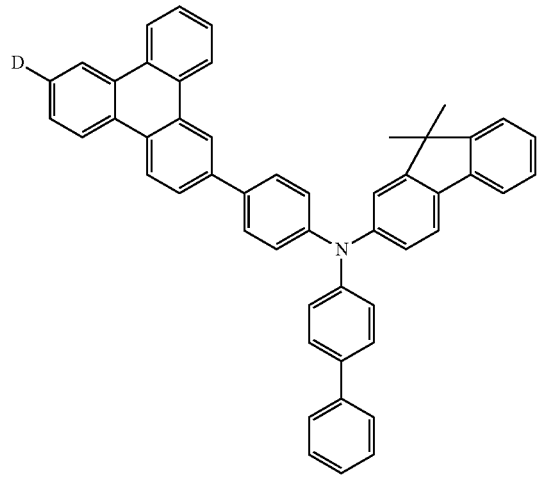
[Formula 1-15]
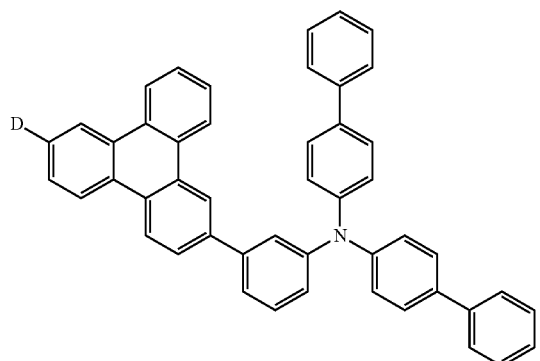
[Formula 1-16]
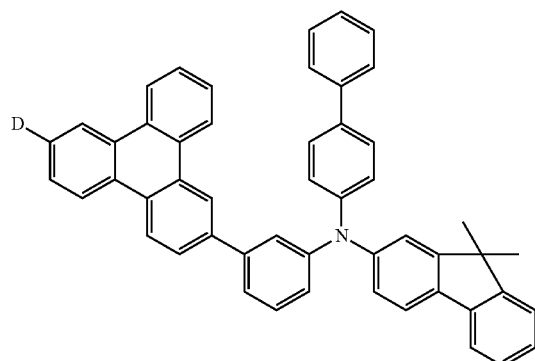
[Formula 1-17]
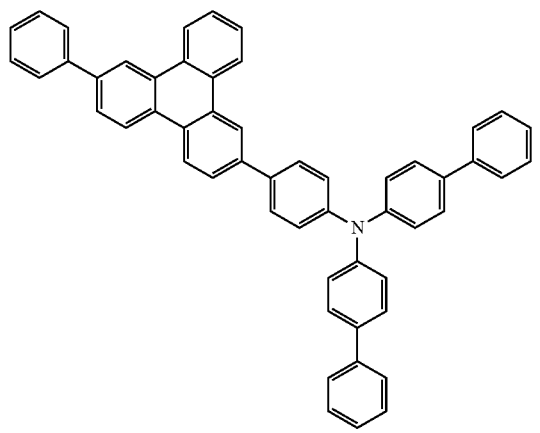
[Formula 1-18]
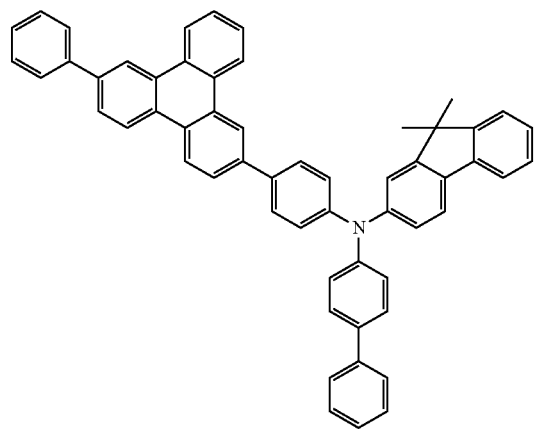

-continued
[Formula 1-19]
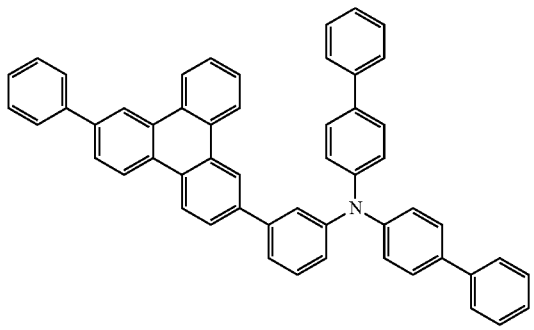
[Formula 1-20]
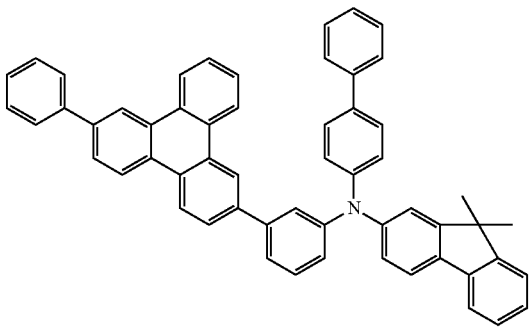
[Formula 1-21]
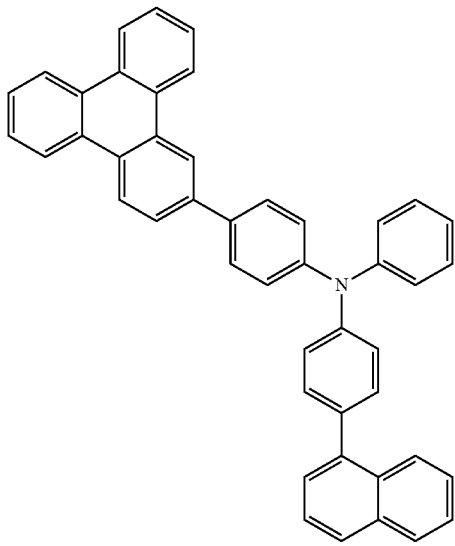
[Formula 1-22]
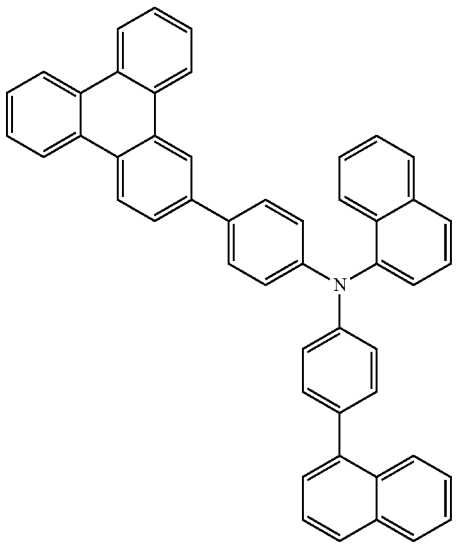
[Formula 1-23]
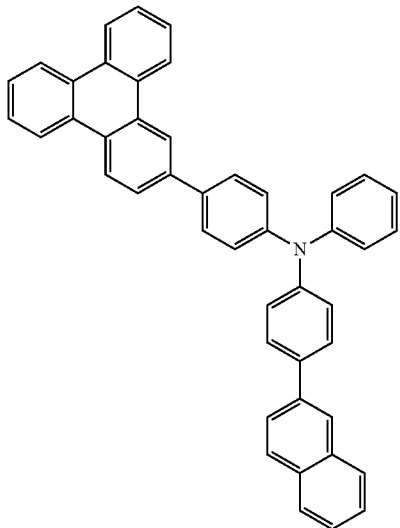
[Formula 1-24]
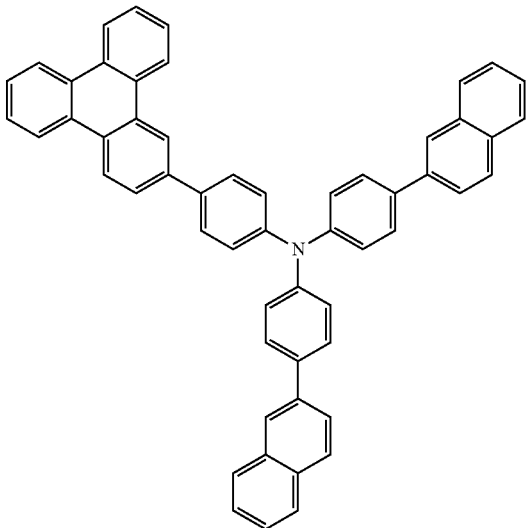

-continued
[Formula 1-25]
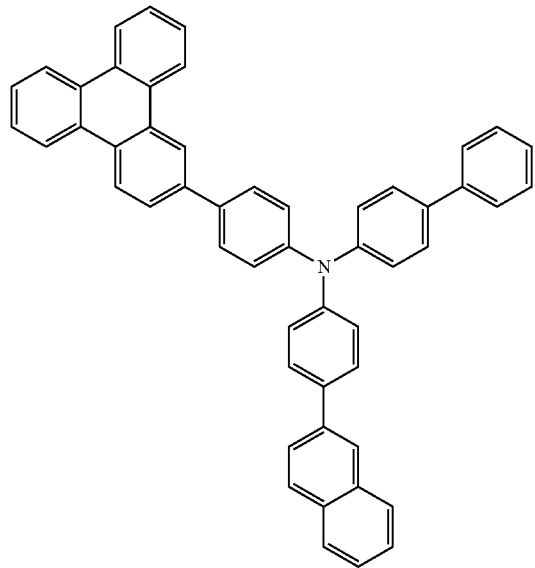
[Formula 1-26]
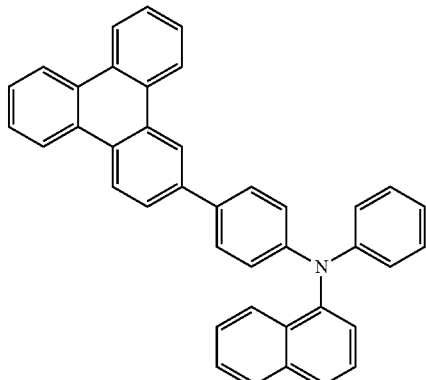
[Formula 1-27]
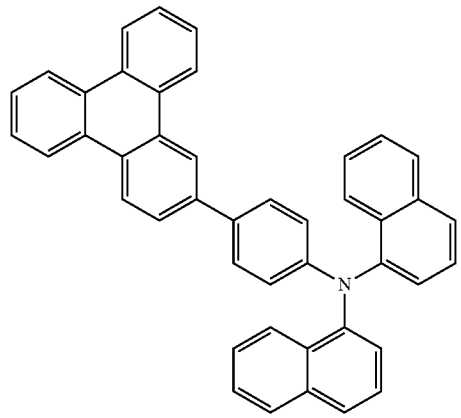
[Formula 1-28]
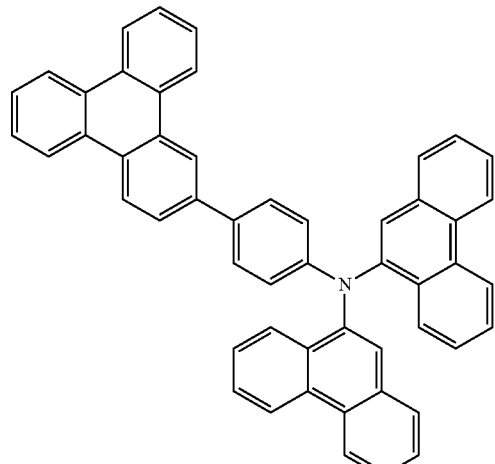
[Formula 1-29]
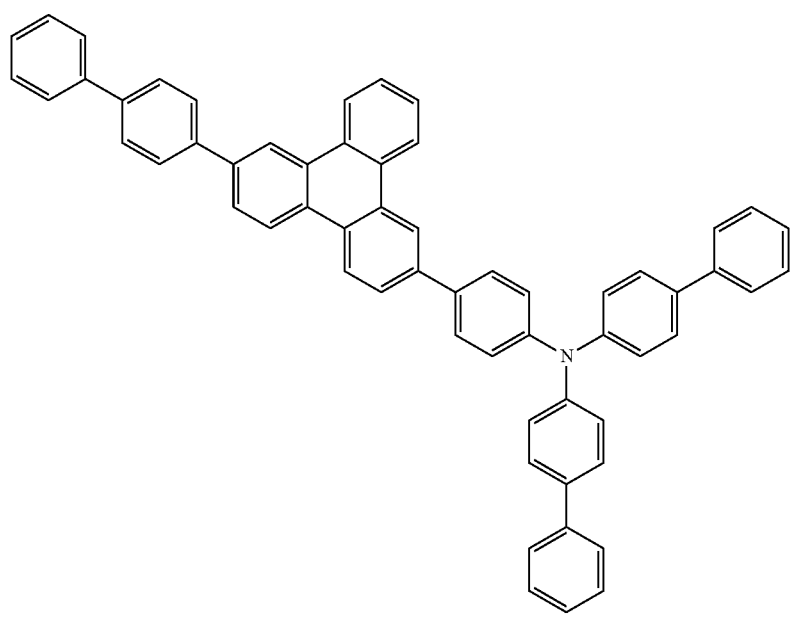

[Formula 1-30]
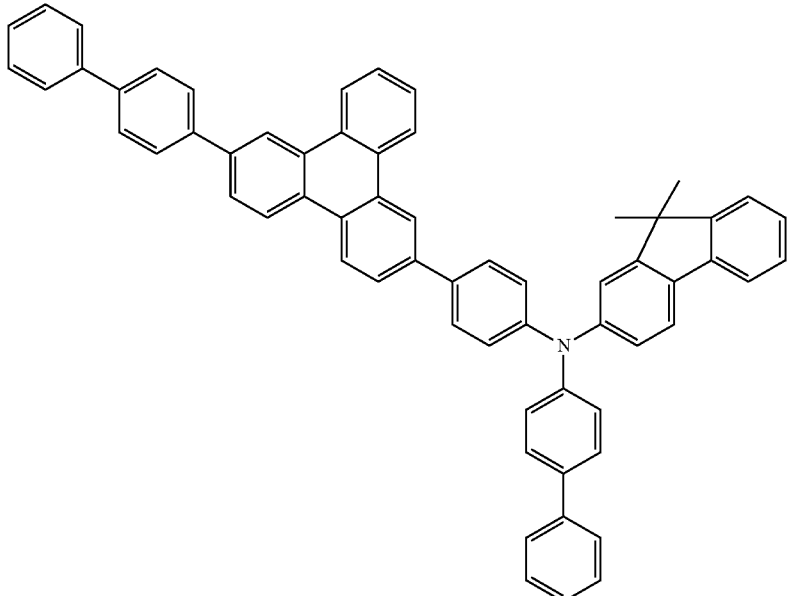
[Formula 1-31]
[Formula 1-32]
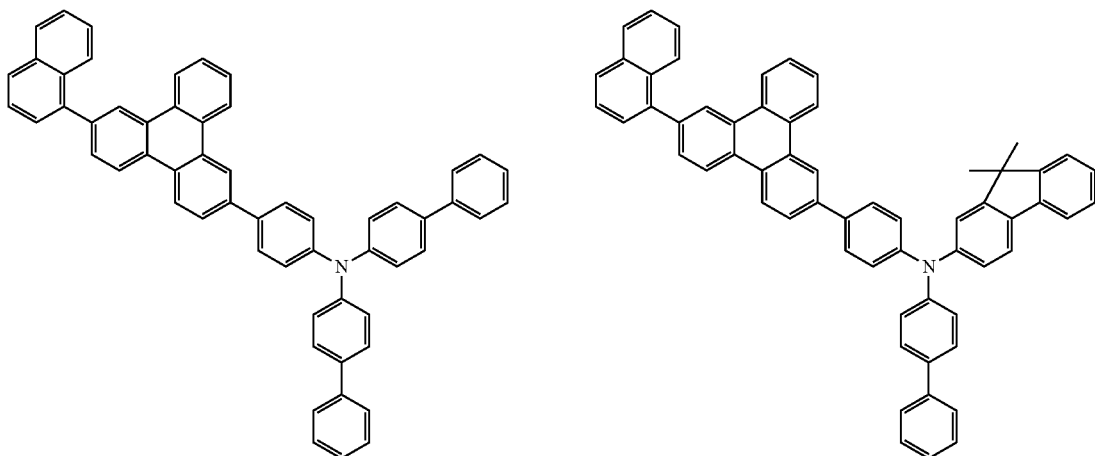
[Formula 1-33]
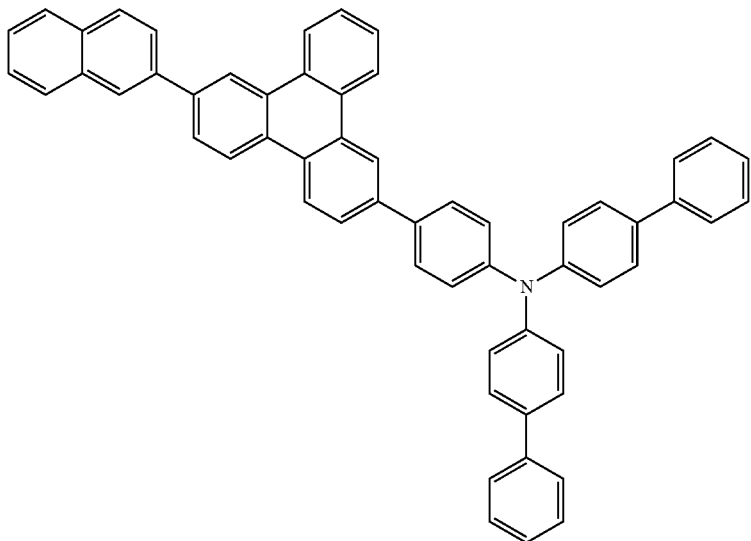

[Formula 1-34]
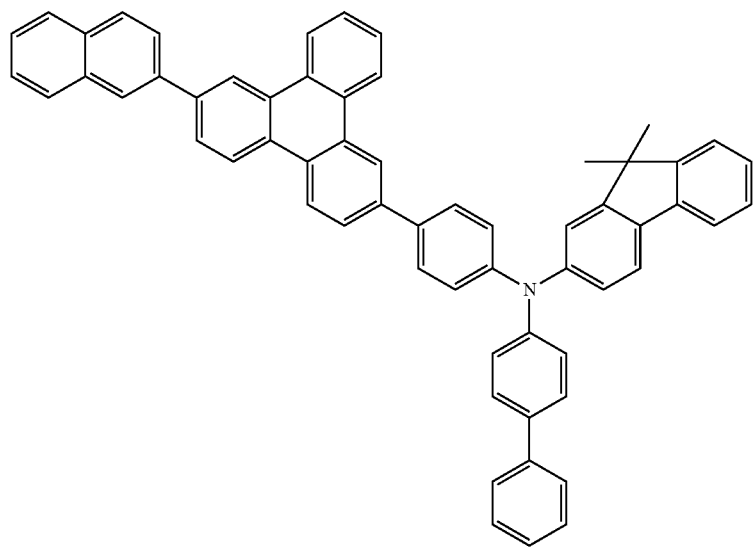
[Formula 1-35]
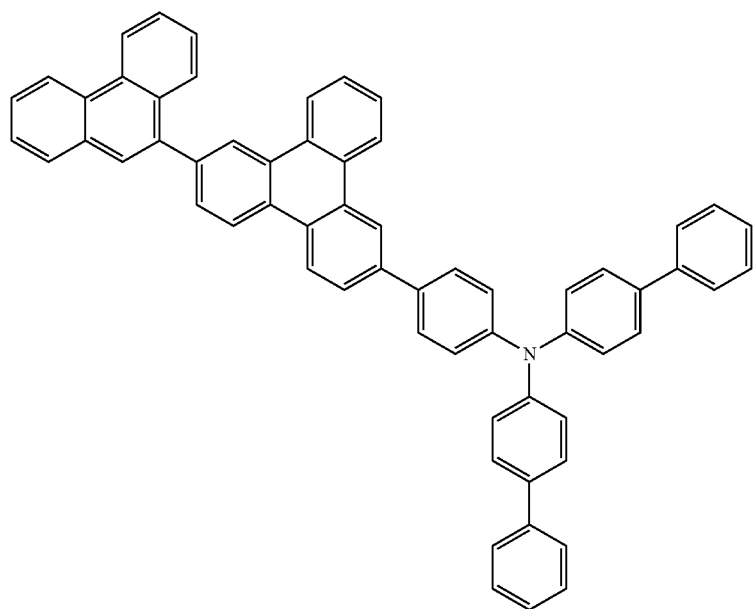

[Formula 1-36]
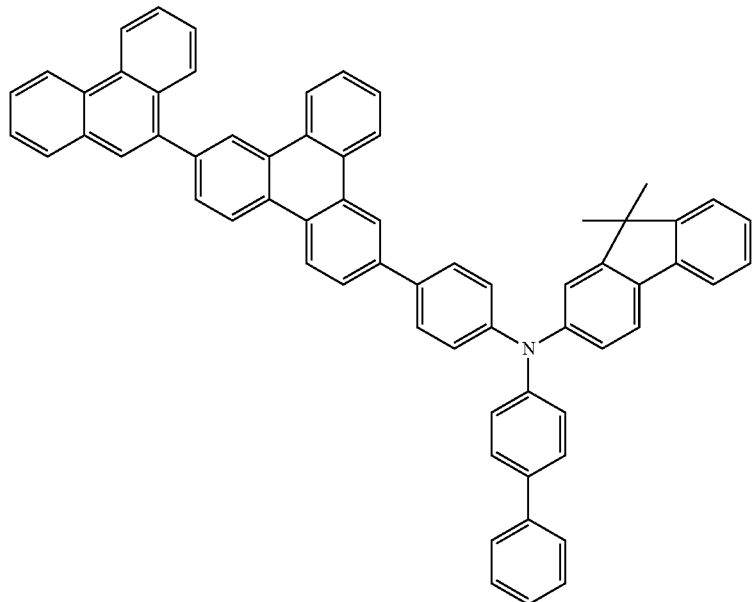
[Formula 1-37]
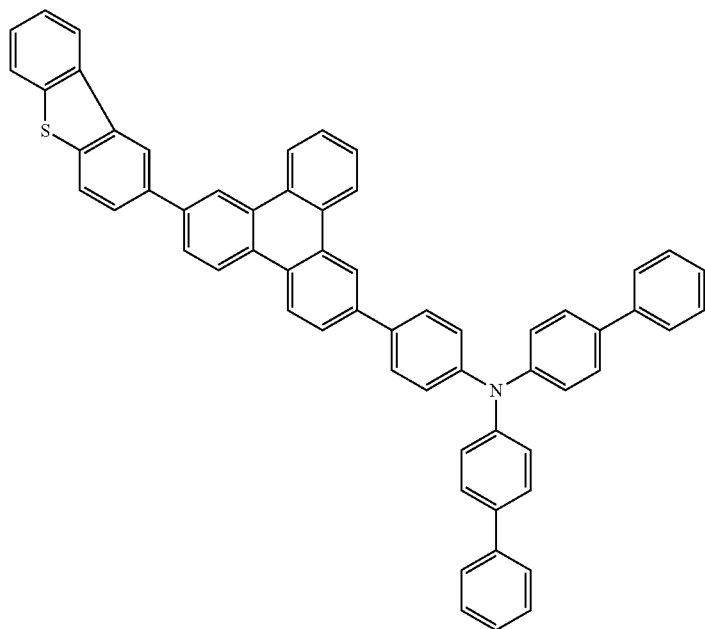

[Formula 1-38]
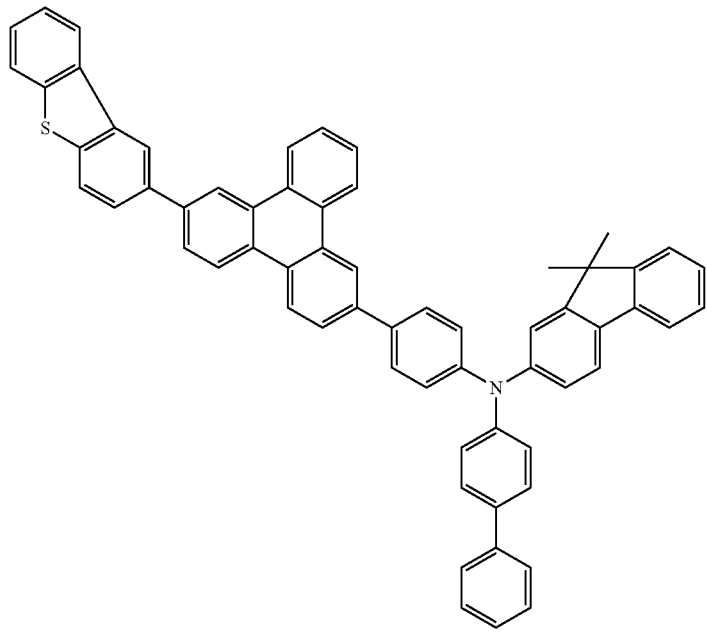
[Formula 1-39]
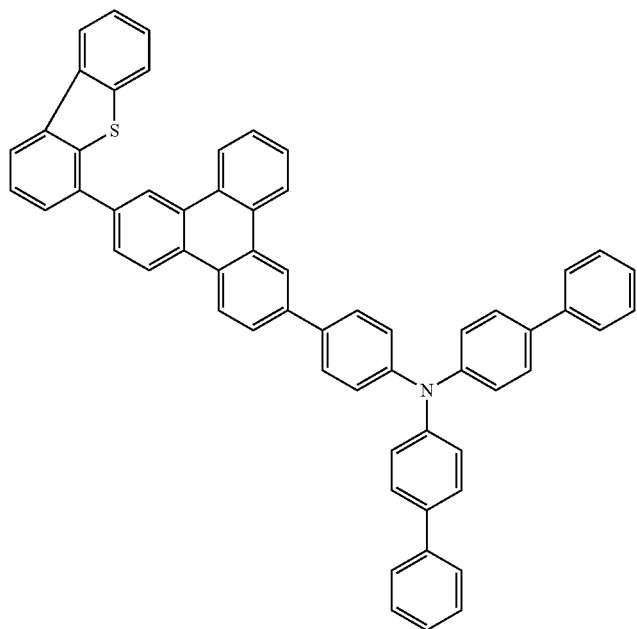

[Formula 1-40]
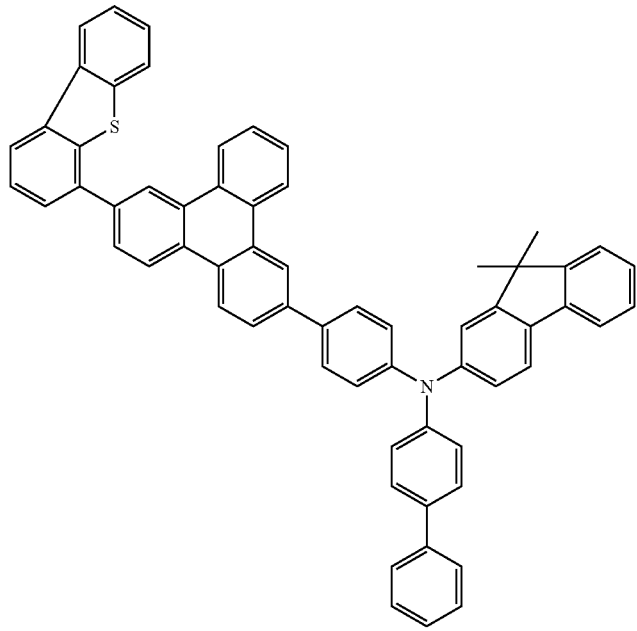
[Formula 1-41]
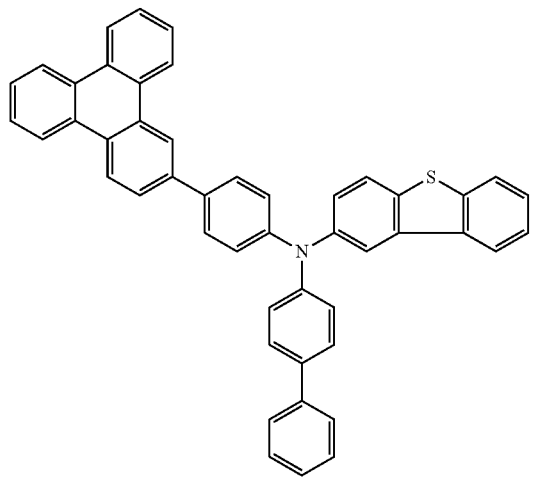
[Formula 1-42]
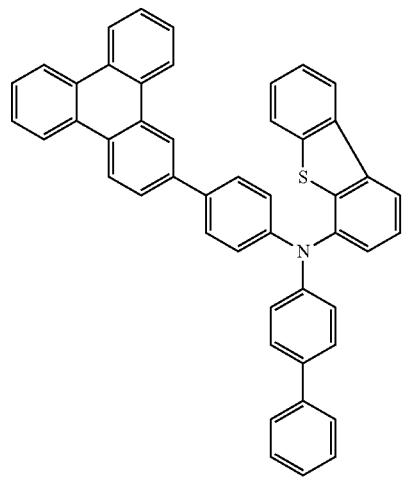
[Formula 1-43]
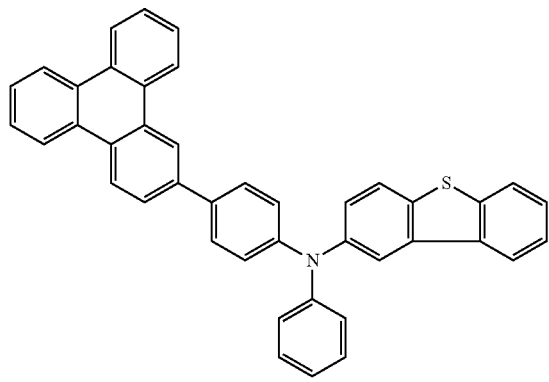
[Formula 1-44]
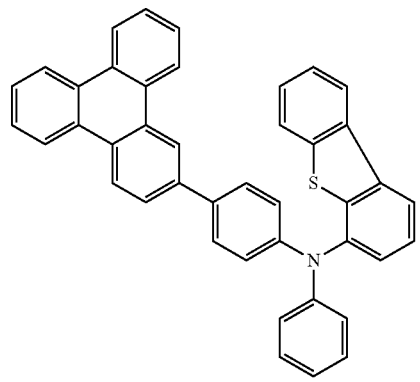

[Formula 1-45]
[Formula 1-46]
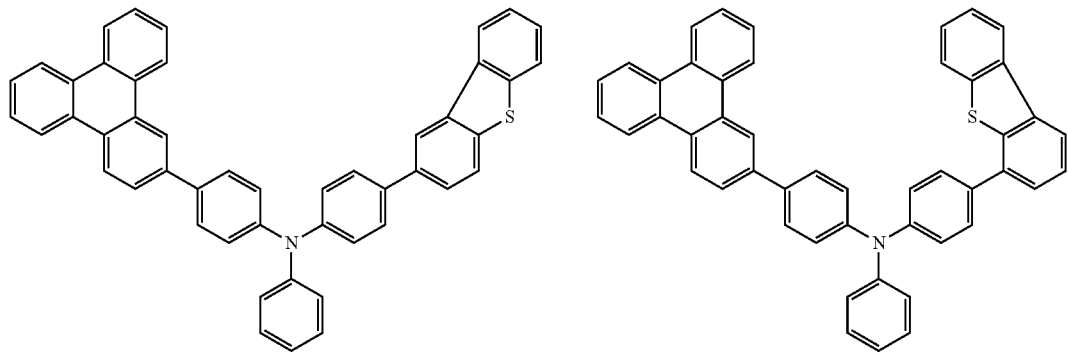
[Formula 1-47]
[Formula 1-48]
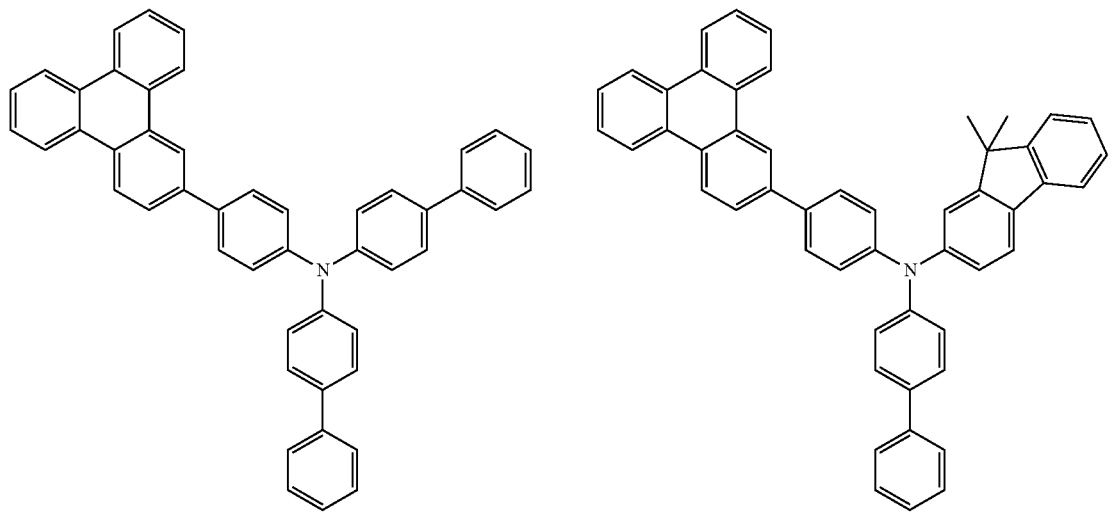
[Formula 1-49]
[Formula 1-50]
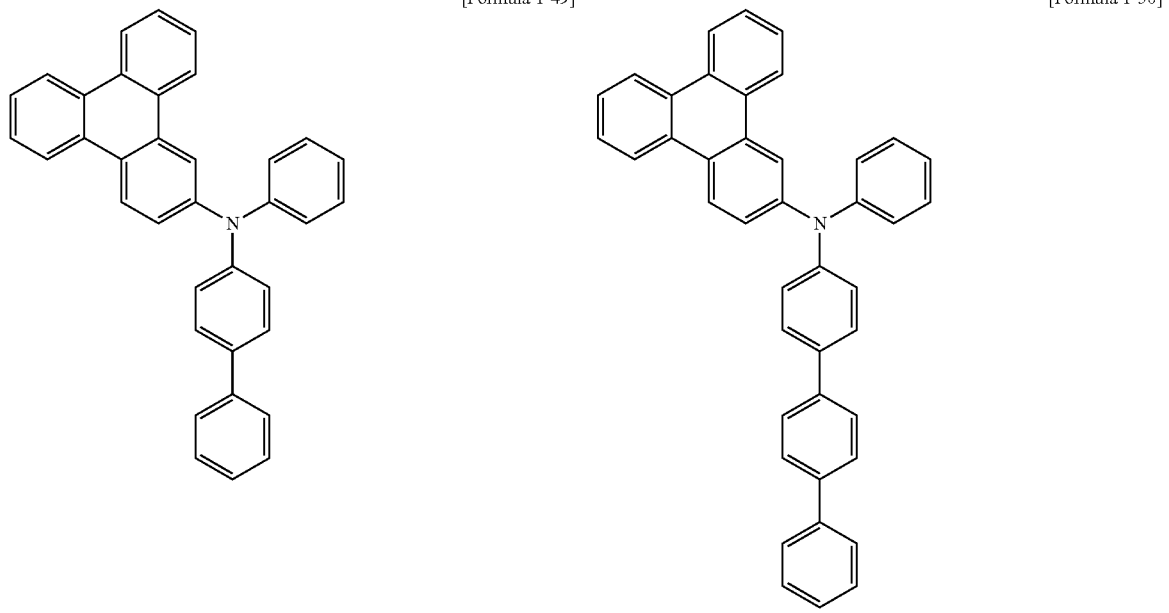

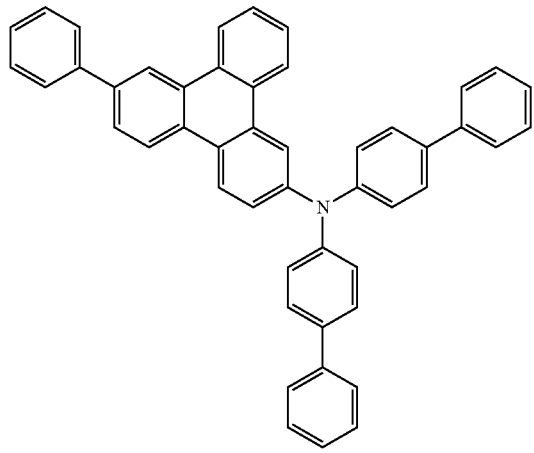

[Formula 1-51]

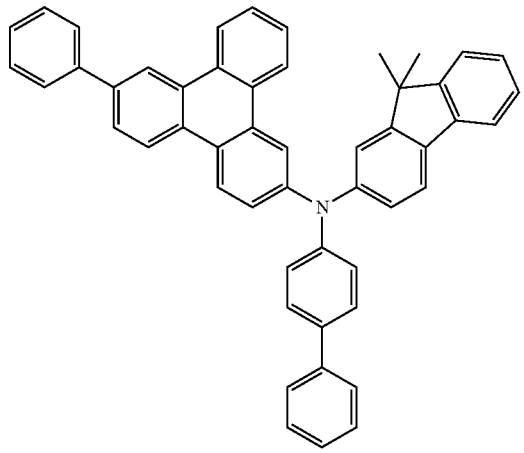

[Formula 1-52]

In addition, the present invention provides a preparation method of a derivative represented by the above Formula 1. The compound represented by Formula 1 may be prepared by general methods known in the art, such as condensation reaction, Suzuki coupling reaction, and the like.

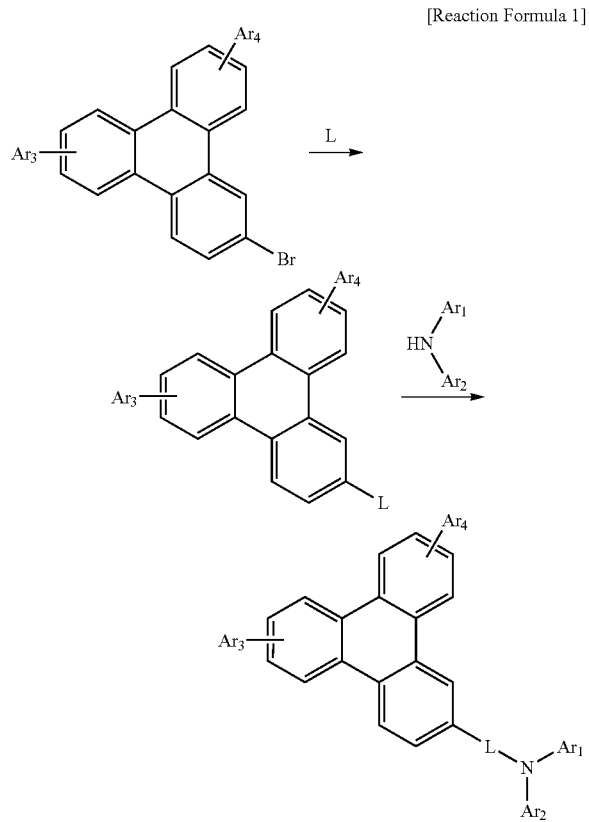

[Reaction Formula 1]

In Reaction Formula 1, L and $Ar_1$ to $Ar_4$ are the same as those defined in Formula 1.

The compound of Formula 1 according to the present invention may be prepared in multi-step chemical reactions. The preparation of the compounds is described in the following Preparation Examples. As shown in Preparation Examples, some intermediate compounds are first prepared and compounds of Formula 1 are prepared from the intermediate compounds.

The compounds represented by Formula 1 may have characteristics appropriate for use as an organic material layer used in an organic light emitting device by introducing various substituents into a core structure shown in the Formula.

The compound represented by Formula 1 has a high glass transition temperature (Tg), and thus has excellent thermal stability. The improvement in thermal stability is an important factor which provides the driving stability to a device.

In addition, the organic light emitting device according to the present invention comprises an organic light emitting device comprising a first electrode, a second electrode, and an organic material layer having one or more layers disposed between the first electrode and the second electrode, wherein one or more layers of the organic material layer comprise a compound represented by the above Formula 1.

The organic light emitting device of the present invention may be prepared by using typical methods and materials for manufacturing an organic light emitting device, except that an organic material layer having one or more layers is formed by using the above-described compounds.

The compound represented by Formula 1 may be used to form an organic material layer by using a solution coating method as well as a vacuum deposition method during the manufacture of an organic light emitting device. As used herein, the solution coating method refers to spin coating, dip coating, inkjet printing, screen printing, a spray method, roll coating, and the like, but is not limited thereto.

The organic material layer of the organic light emitting device of the present invention may be composed of a mono-layer structure, but may be composed of a multi-layer structure in which organic material layers having two or more layers are stacked. For example, the organic light emitting device of the present invention may have a structure comprising a hole injection layer, a hole transporting layer, a light emitting layer, an electron transporting layer, an electron injection layer, and the like as an organic material layer. However, the structure of the organic light emitting device is not limited thereto, and may comprise the fewer number of organic material layers.

Accordingly, in the organic light emitting device of the present invention, the organic material layer may comprise one or more layers of a hole injection layer, a hole transporting layer, and a layer which injects and transports holes simultaneously, and one or more layers of the layers may comprise the compound represented by Formula 1.

Further, the organic material layer may comprise a light emitting layer, and the light emitting layer may comprise the compound represented by Formula 1.

In addition, the organic material layer may comprise one or more layers of an electron transporting layer, an electron injection layer, and a layer which transports and injects electrons simultaneously, and one or more layers of the layers may comprise the compound represented by Formula 1.

In the organic material layer having the multi-layer structure, the compound represented by Formula 1 may be contained in a light emitting layer, a layer which injects/transports holes and emits light simultaneously, a layer which transports holes and emits light simultaneously, or a layer which transports electrons and emits light simultaneously.

Figure 2:
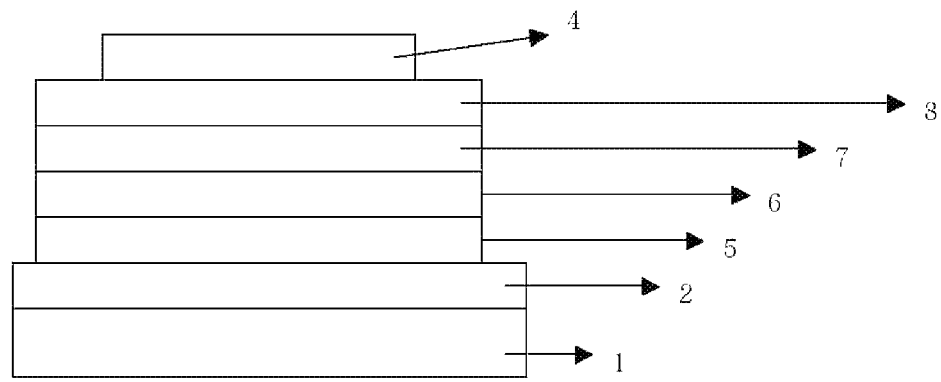
FIG. 2 illustrates an example of an organic light emitting device comprising a substrate 1, a positive electrode 2, a hole injection layer 5, a hole transporting layer 6, a light emitting layer 7, an electron transporting layer, and a negative electrode 4.

For example, the organic light emitting device of the present invention may have structures shown in FIGS. 1 and 2, but is not limited thereto.

In FIG. 1, the structure of an organic light emitting device, in which a positive electrode 2, a light emitting layer 3, and a negative electrode 4 are sequentially stacked on a substrate 1, is illustrated. In the structure, the compound represented by Formula 1 may be contained in the light emitting layer 3.

In FIG. 2, the structure of an organic light emitting device, in which a positive electrode 2, a hole injection layer 5, a hole transporting layer 6, a light emitting layer 7, an electron transporting layer, and a negative electrode 4 are sequentially stacked on a substrate 1, is illustrated. In the structure, the compound represented by Formula 1 may be contained in the hole injection layer 5, the hole transporting layer 6, the light emitting layer 7, or the electron transporting layer 8.

For example, the organic light emitting device according to the present invention may be manufactured by depositing a metal or a metal oxide having conductivity, or an alloy thereof on a substrate to form a positive electrode, forming an organic material layer which comprises a hole injection layer, a hole transporting layer, a light emitting layer, and an electron transporting layer thereon, and then depositing a material which may be used as the negative electrode thereon by using a physical vapor deposition (PVD) method such as sputtering or e-beam evaporation. In addition to these methods, an organic light emitting device may be manufactured by sequentially depositing a negative electrode material, an organic material layer, and a positive electrode material on a substrate.

The organic material layer may be a multi-layer structure comprising the hole injection layer, the hole transporting layer, the light emitting layer, the electron transporting layer, and the like, but may be a mono-layer structure without being limited thereto. Further, the organic material layer may be manufactured with fewer layers by using various polymer materials by a solvent process other than a deposition method, for example, methods, such as spin coating, dip coating, doctor blading, screen printing, inkjet printing, or thermal transfer method, and the like.

The positive electrode materials are preferably materials having large work function for usually facilitating the injection of holes into the organic material layer. Specific examples of the positive material which may be used in the present invention comprise metals such as vanadium, chromium, copper, zinc, and gold, or alloys thereof; metal oxides such as zinc oxide, indium oxide, indium tin oxide (ITO), and indium zinc oxide (IZO); a combination of metal and oxide, such as ZnO:Al or $SnO_2$:Sb; and electrically conductive polymers, such as poly(3-methylcompound), poly[3,4-(ethylene-1,2-dioxy)compound] (PEDT), polypyrrole, and polyaniline, and the like, but are not limited thereto.

The negative electrode materials are preferably materials having small work function for usually facilitating the injection of electrons into the organic material layer. Specific examples of the negative electrode material comprise metals such as metals such as magnesium, calcium, sodium, potassium, titanium, indium, yttrium, lithium, gadolinium, aluminum, silver, tin and lead or alloys thereof; multilayer structured materials such as LiF/Al or $LiO_2$/Al, and the like, but are not limited thereto.

The hole injection materials are materials facilitating hole injection from the positive electrode at low voltage. The HOMO (highest occupied molecular orbital) of the hole injecting material is preferably located between the work function of the positive electrode materials and the HOMO of its neighboring organic material layer. Specific examples of the hole injecting material comprise metal porphyrine, oligothiophene, arylamine-based organic materials, hexanitrile hexaazatriphenylene-based organic materials, quinacridone-based organic materials, perylene-based organic materials, antraquinone, and polyaniline-based and polycompound-based conductive polymers, but are not limited thereto.

The hole transporting materials are suitably materials having high hole mobility, which may accept holes from the positive electrode or the hole injection layer and transfer the holes toward the light emitting layer. Specific examples thereof comprise arylamine-based organic materials, conductive polymers, block copolymers having both conjugated portions and non-conjugated portions, and the like, but are not limited thereto.

The light emitting materials are materials capable of emitting light in a visible light region by accepting and recombining holes from the hole transporting layer and electrons from the electron transporting layer, respectively, and preferably a material having high quantum efficiency for fluorescence or phosphorescence. Specific examples thereof comprise a 8-hydroxyquinoline-aluminum complex ($Alq_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene)(PPV)-based polymers; spiro compounds; and polyfluorene, rubrene, and the like, but are not limited thereto.

The electron transporting materials are suitably materials having high electron mobility, which may accept electrons from the negative electrode and transfer the electrons to the light emitting layer. Specific examples thereof comprise aluminum complexes of 8-hydroxyquinoline; complexes comprising $Alg_3$; organic radical compounds; hydroxyflavone-metal complexes, and the like, but are not limited thereto.

The organic light emitting device according to the present invention may be of a top emission type, a bottom emission type or a top and bottom emission type according to the materials used.

In the compound according to the present invention, principles, which are applied to organic light emitting device s, may be also applied to organic electronic devices comprising organic solar cells, organic photoconductors, organic transistors, and the like in the similar manner.

The preparation method of the compound of Formula 1 and the manufacture of an organic light emitting device using the same will be described in detail in the following Preparation Examples and Examples. However, the following Preparation Examples and Examples are provided for illustrative purposes only, and the scope of the present invention should not be limited thereto.

EXAMPLE

Synthetic Example 1

Preparation of the Compound Represented by Formula 1-1

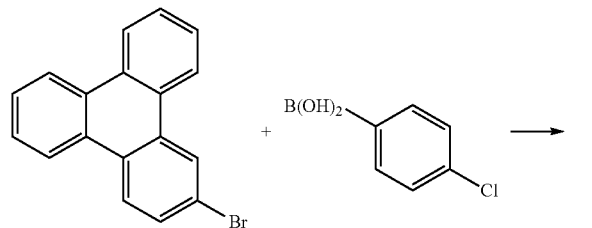

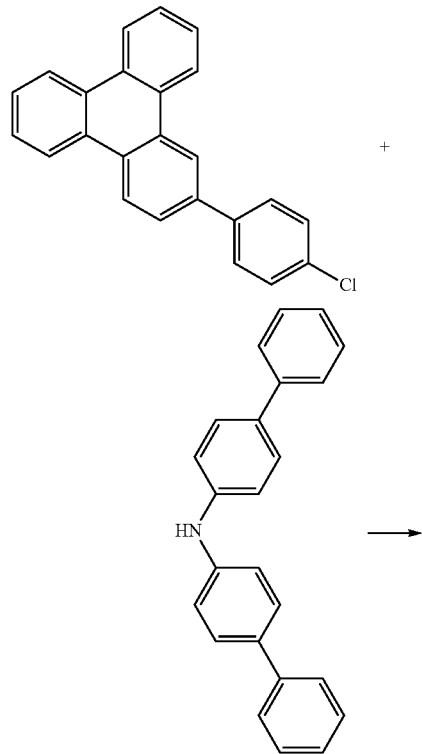

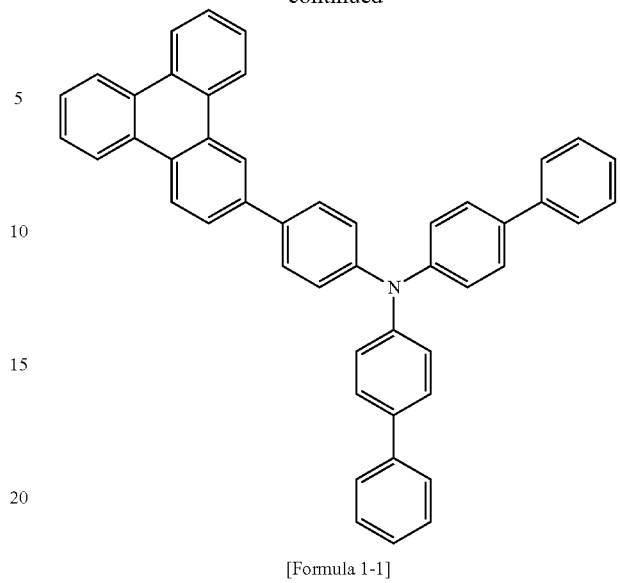

[Formula 1-1]

1) Preparation of Formula 1A 2-bromotriphenylene (30 g, 97.7 mmol) and 4-chlorophenyl boronic acid (16.7 g, 107 mmol) were dissolved in tetrahydrofuran (150 ml), and potassium carbonate ($K_2CO_3$, 40.4 g, 292.8 mmol) and water were added to the resulting reaction solution, followed by heating while stirring under a nitrogen atmosphere for 1 hr. After the heating while stirring for 1 hour was completed, tetrakis(triphenylphosphine)palladium (2.3 g, 1.95 mmol) was added thereto, followed by heating while stirring for 4 hr. After the reaction was completed, the temperature was lowered to normal temperature, and tetrahydrofuran was removed by distillation under reduced pressure, dissolved in chloroform and dried over anhydrous magnesium sulfate. The solution was distilled under reduced pressure and recrystallized with tetrahydrofuran and ethanol to obtain a compound of Formula 1A (27 g, yield 82%).

MS: $[M+H]^+=339$

2) Preparation of Formula 1-1

The compound of Formula 1A (10 g, 29.5 mmol) and bisdiphenylamine (9.96 g, 31 mmol) were dissolved in 150 ml of xylene, sodium-tertiary-butoxide (5.67 g, 59 mmol) and bis[(tri-tertiary-butyl)phosphine]palladium ($Pd[P(t-Bu)_3]_2$) (0.45 g, 0.89 mmol) were added thereto, followed by refluxing under a nitrogen atmosphere for 3 hr. After the reaction was completed, it was lowered to normal temperature and the produced solid was filtered. The filtered solid was dissolved in chloroform, distilled under reduced pressure, and recrystallized with tetrahydrofuran and ethanol to obtain a compound of Formula 1-1 (8 g, 44%).

MS: $[M+H]^+=624$

Synthetic Example 2

Preparation of the Compound Represented by Formula 1-2

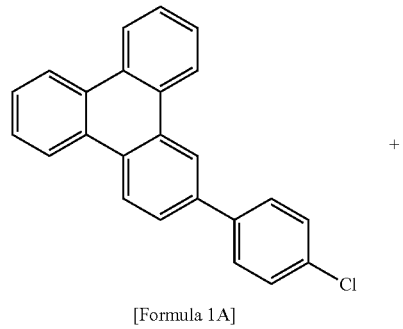

[Formula 1A]

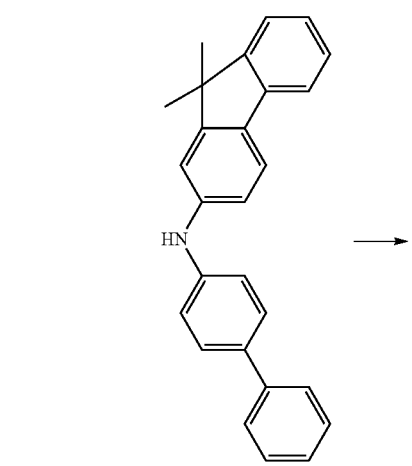

[Formula 1-2]

A compound 1-2 (9 g, 46%) was obtained in the same manner as in preparation of the compound 1-1 in Synthetic Example 1, except that the compound diphenyl-fluorene amine (11.2 g, 31 mmol) was used instead of the compound bisdiphenylamine.

MS: $[M+H]^+=664$

Synthetic Example 3

Preparation of the Compound Represented by Formula 1-3

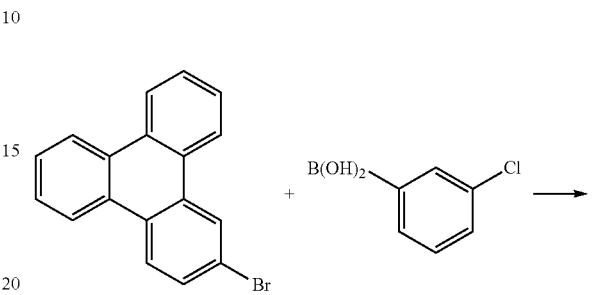

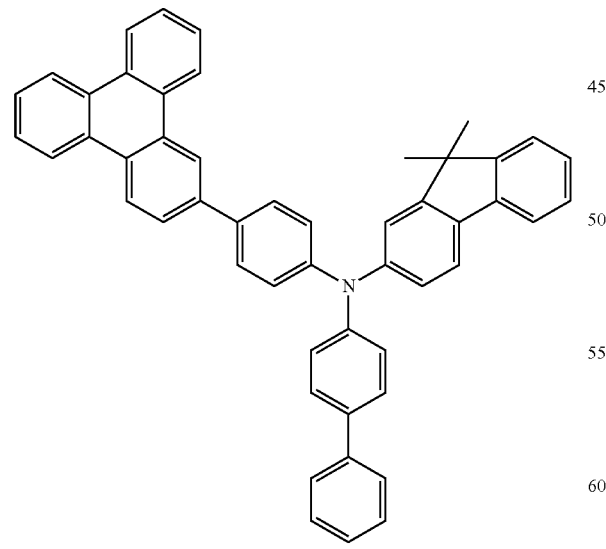

[Formula 1B]

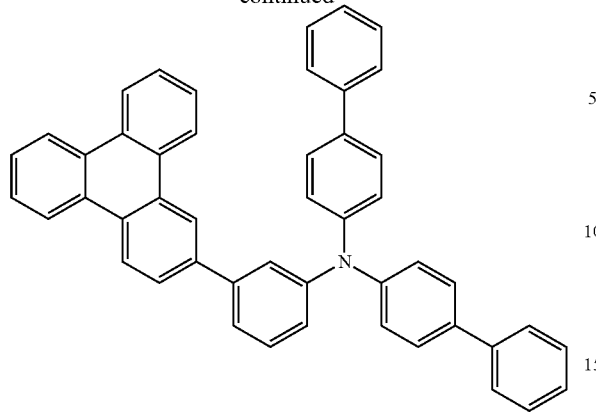

[Formula 1-3]

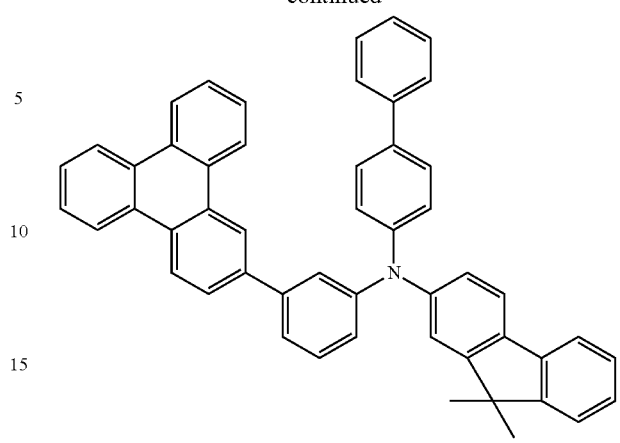

[Formula 1-4]

1) Preparation of Formula 1B

A compound 1B (25 g, yield 76%) was obtained in the same manner as in preparation of the compound 1A in Synthetic Example 1, except that the compound 3-chlorophenyl boronic acid (16.7 g, 107 mmol) was used instead of the compound 4-chlorophenyl boronic acid.

MS: [M+H]$^+$=339

2) Preparation of Formula 1-3

A compound 1-3 (7.9 g, yield 43%) was obtained in the same manner as in preparation of the compound 1-1 in Synthetic Example 1, except that the compound 1B (10 g, 29.5 mmol) was used instead of the compound 1A.

MS: [M+H]$^+$=624

A compound 1-4 (12 g, 61%) was obtained in the same manner as in preparation of the compound 1-3 in Synthetic Example 3, except that the compound diphenyl-fluorene amine (11.2 g, 31 mmol) was used instead of the compound bisdiphenylamine.

MS: [M+H]$^+$=664

Synthetic Example 5

Preparation of the Compound Represented by Formula 1-7

Synthetic Example 4

Preparation of the Compound Represented by Formula 1-4

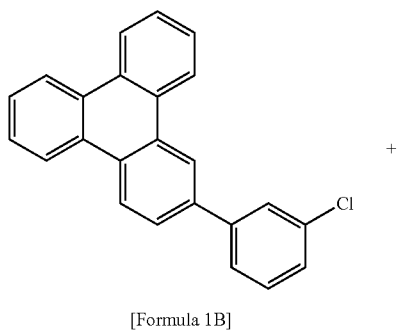

[Formula 1B]

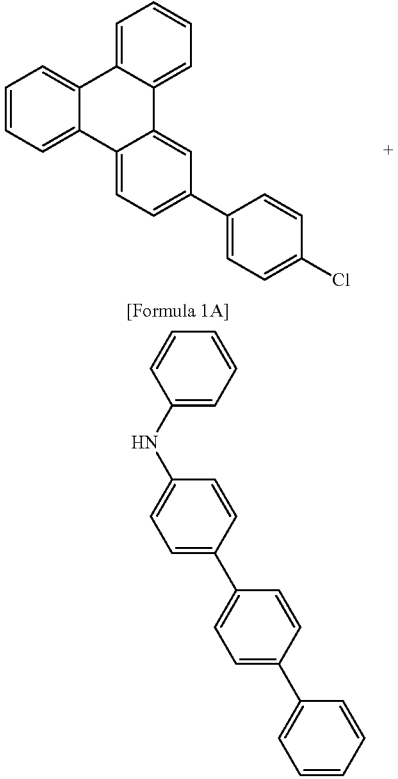

[Formula 1A]

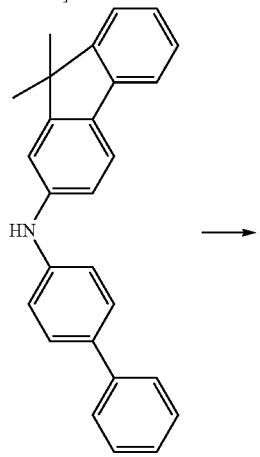

-continued

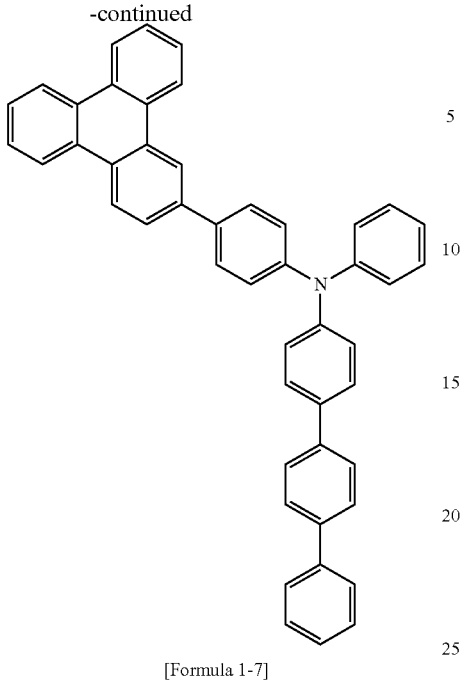

[Formula 1-7]

A compound 1-7 (13 g, 70.6%) was obtained in the same manner as in preparation of the compound 1-1 in Synthetic Example 1, except that the compound terphenylphenyl amine (9.96 g, 31 mmol) was used instead of the compound bis-diphenylamine.

MS: [M+H]$^+$=624

Synthetic Example 6

Preparation of the Compound Represented by Formula 1-8

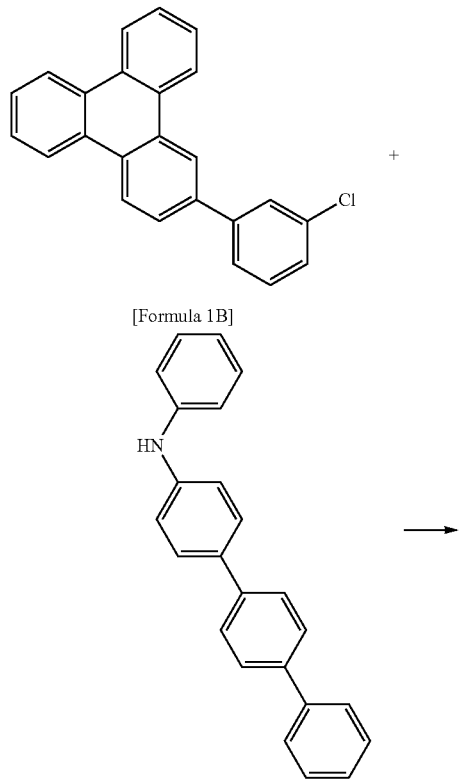

-continued

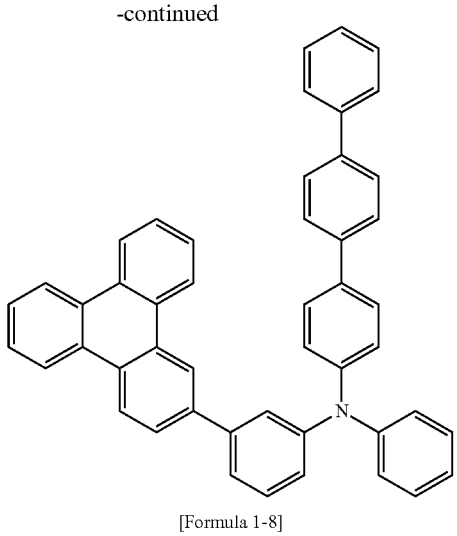

[Formula 1-8]

A compound 1-8 (11 g, 60%) was obtained in the same manner as in preparation of the compound 1-3 in Synthetic Example 3, except that the compound terphenyl amine (9.96 g, 31 mmol) was used instead of the compound bisdiphenylamine.

MS: [M+H]$^+$=624

Synthetic Example 7

Preparation of the Compound Represented by Formula 1

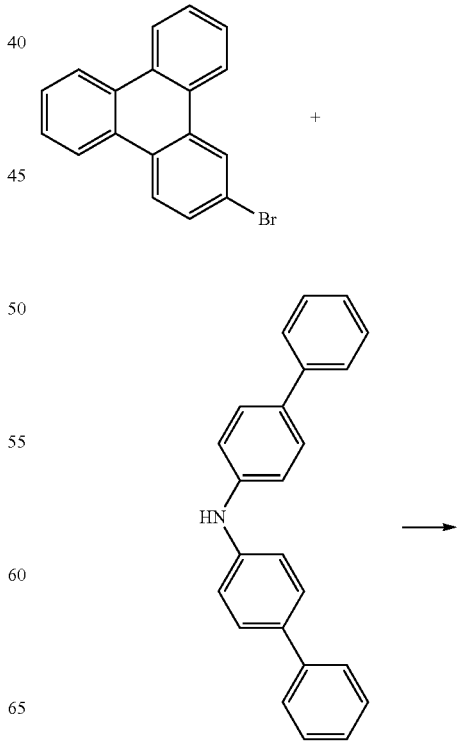

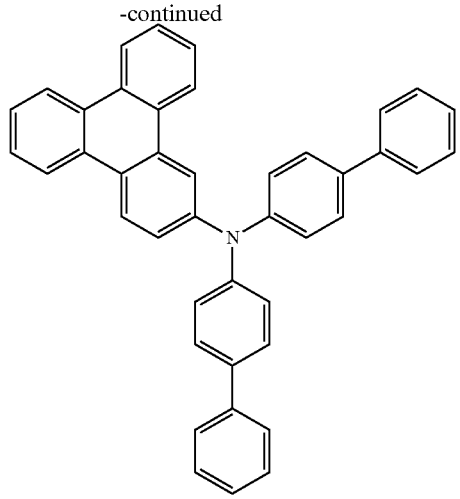

[Formula 1-47]

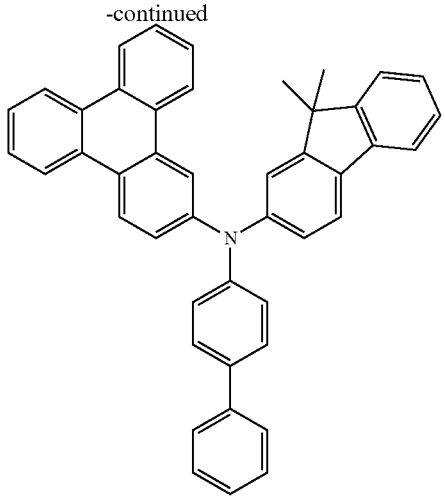

[Formula 1-48]

2-bromotriphenylene (10 g, 32.6 mmol) and bisdiphenyl amine (11 g, 34.2 mmol) were dissolved in 150 ml of toluene, sodium-tertiary-butoxide (6.26 g, 65.2 mmol) and bis[(tri-tertiary-butyl)phosphine]palladium (Pd[P(t-Bu)$_3$]$_2$) (0.5 g, 0.98 mmol) were added thereto, followed by refluxing under a nitrogen atmosphere for 3 hr. After the reaction was completed, it was lowered to normal temperature and the produced solid was filtered. The filtered solid was dissolved in chloroform, distilled under reduced pressure, and recrystallized with tetrahydrofuran and ethanol to obtain a compound of Formula 1-47 (12 g, 67%).

MS: [M+H]$^+$=547

Synthetic Example 8

Preparation of the Compound Represented by Formula 1-48

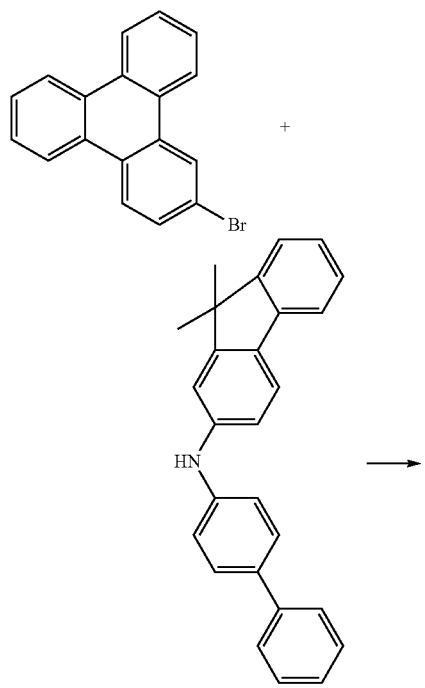

A compound 1-48 (11 g, 57%) was obtained in the same manner as in preparation of the compound 1-47 in Synthetic Example 7, except that the compound diphenyl-fluorene amine (11.8 g, 34.2 mmol) was used instead of the compound bisdiphenylamine.

MS: [M+H]$^+$=587

Example 1

A glass substrate, on which indium tin oxide (ITO) was coated to a thickness of 1000 Å to form a thin film, was put in a distilled water, in which a dispersing agent was dissolved, and then washed using ultrasonic waves. A product manufactured by Fischer Co. was used as a detergent, and distilled water twice filtered by using a filter manufactured by Millipore Co. was used. After ITO was washed for 30 min, ultrasonic washing was twice conducted by using distilled water for 10 min. After the washing using distilled water was completed, ultrasonic washing was conducted using isopropyl alcohol, acetone, and methanol solvents in sequence, and drying was then conducted.

Hexanitrile hexaazatriphenylene was vacuum deposited to a thickness of 500 Å by heating on a transparent ITO electrode, which was thus prepared, so as to form a hole injection layer. The compound of Formula 1-1 (400 Å), which was synthesized above in Preparation Example 1, as a material for transporting holes was vacuum deposited thereon, and a host H1 and a dopant D1 compound were vacuum deposited to a thickness of 300 Å as a light emitting layer. Next, the E1 compound (300 Å) was vacuum deposited sequentially as electron injection and transporting layers by heating. An organic light emitting device was manufactured by sequentially depositing lithium fluoride (LiF) having a thickness of 12 Å and aluminum having a thickness of 2,000 Å on the electron transporting layer to form a negative electrode.

In the above-described procedure, the deposition rate of organic materials was maintained at 1 Å/sec, while the deposition rates of lithium fluoride and aluminum were maintained at 0.2 Å/sec and 3 to 7 Å/sec, respectively.

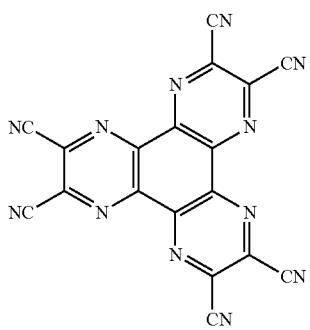

[Hexanitrile hexaazatriphenylene]

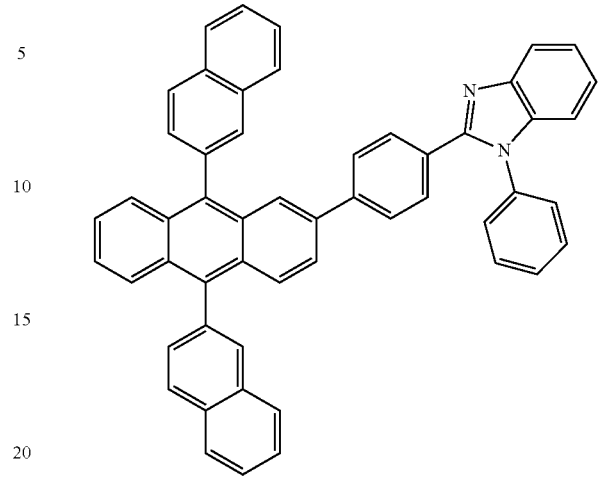

[E1]

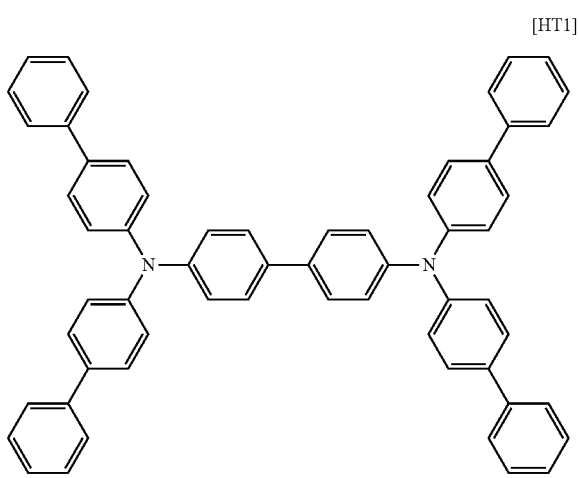

[HT1]

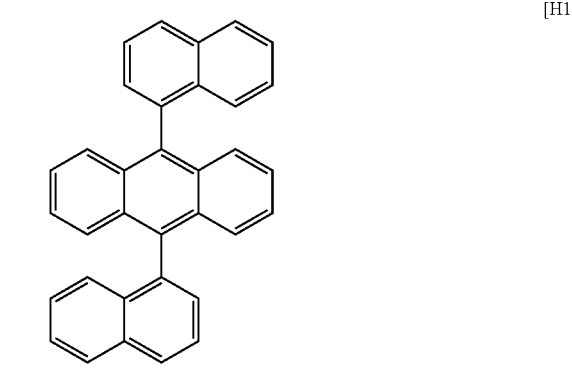

[H1]

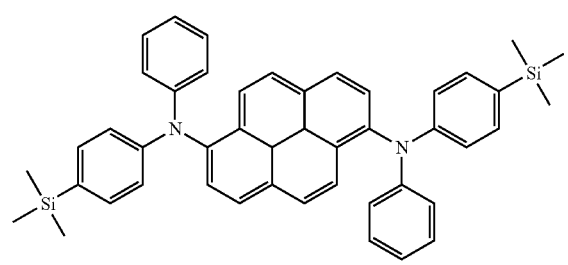

[D1]

Example 2

An experiment was performed in the same manner as in Example 1, except that the compound of Formula 1-2 was used as the hole transporting layer instead of the compound of Formula 1-1 synthesized in Preparation Example 1.

Example 3

An experiment was performed in the same manner as in Example 1, except that the compound of Formula 1-3 was used as the hole transporting layer instead of the compound of Formula 1-1 synthesized in Preparation Example 1.

Example 4

An experiment was performed in the same manner as in Example 1, except that the compound of Formula 1-4 was used as the hole transporting layer instead of the compound of Formula 1-1 synthesized in Preparation Example 1.

Example 5

An experiment was performed in the same manner as in Example 1, except that the compound of Formula 1-7 was used as the hole transporting layer instead of the compound of Formula 1-1 synthesized in Preparation Example 1.

Example 6

An experiment was performed in the same manner as in Example 1, except that the compound of Formula 1-8 was used as the hole transporting layer instead of the compound of Formula 1-1 synthesized in Preparation Example 1.

Example 7

An experiment was performed in the same manner as in Example 1, except that the compound of Formula 1-47 was used as the hole transporting layer instead of the compound of Formula 1-1 synthesized in Preparation Example 1.

Example 8

An experiment was performed in the same manner as in Example 1, except that the compound of Formula 1-48 was used as the hole transporting layer instead of the compound of Formula 1-1 synthesized in Preparation Example 1.

Comparative Example 1

An experiment was performed in the same manner as in Example 1, except that HT1 was used as the hole transporting layer instead of the compound of Formula 1-1 synthesized in Preparation Example 1

Each compound was used as a hole transporting layer material as in Examples 1 to 8 and Comparative Example 1 to manufacture an organic light emitting device, on which experiment was performed, and the results thereof are shown in Table 1.

TABLE 1

| Experimental Example 50 mA/cm$^2$ | HTL material | Voltage (V) | Current efficiency |
|---|---|---|---|
| Comparative Example 1 | HT1 | 6.14 | 5.87 |
| Example 1 | Formula 1-1 | 6.25 | 6.46 |
| Example 2 | Formula 1-2 | 6.14 | 6.75 |
| Example 3 | Formula 1-3 | 6.28 | 6.62 |
| Example 4 | Formula 1-4 | 6.16 | 6.91 |
| Example 5 | Formula 1-7 | 6.23 | 7.12 |
| Example 6 | Formula 1-8 | 6.23 | 7.20 |
| Example 7 | Formula 1-47 | 6.15 | 7.02 |
| Example 8 | Formula 1-48 | 6.10 | 7.12 |

The compound derivatives of Formulas according to the present invention may serve to inject and transport holes in organic electronic devices comprising organic light emitting device s, and the device according to the present invention shows excellent properties in terms of efficiency, driving voltage, and stability.

The invention claimed is:
1. A compound represented by the following Formula 1:

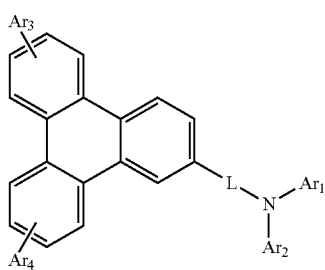

[Formula 1]

wherein
Ar$_1$ is selected from the group consisting of hydrogen; deuterium; an alkyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxy group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryl group which is unsubstituted or substituted by one or more substituent groups selected from the group consisting of a halogen group, an alkyl group, an alkoxy group, a substituted or unsubstituted aryl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a hetero ring group comprising O, N or S as a heteroatom, which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a carbazolyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a fluorenyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; an aryloxy group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; an arylthio group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; and an alkoxycarbonyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group, when Ar₁ is an aryl group, the aryl group is selected from the group consisting of a biphenyl group, terphenyl group, a naphthyl group, an anthracenyl group, a phenanthrene group, a pyrenyl group, a perylenyl group and a chrysenyl group, Ar₂ is selected from the group consisting of hydrogen; deuterium; an alkyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxy group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryl group which is unsubstituted or substituted by one or more substituent groups selected from the group consisting of a halogen group, an alkyl group, an alkoxy group, a substituted or unsubstituted aryl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a hetero ring group comprising O, N or S as a heteroatom, which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a carbazolyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a fluorenyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; an aryloxy group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; an arylthio group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; and an alkoxycarbonyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group, when Ar₂ is an aryl group, the aryl group is selected from the group consisting of a phenyl group, a biphenyl group, terphenyl group, a naphthyl group, an anthracenyl group, a phenanthrene group, a pyrenyl group, a perylenyl group and a chrysenyl group, L is a direct bond; an arylene group having 6 to 40 carbon atoms, which is unsubstituted or substituted by one or more substituent groups selected from the group consisting of nitro, nitrile, halogen, an alkyl group, and an alkoxy group; a divalent hetero ring group which is unsubstituted or substituted by one or more substituent groups selected from the group consisting of nitro, nitrile, halogen, an alkyl group, and an alkoxy group; or a fluorenylene group which is unsubstituted or substituted by one or more substituent groups selected from the group consisting of nitro, nitrile, halogen, an alkyl group, and an alkoxy group, except that L is a direct bond and both of Ar₁ and Ar₂ are a phenyl group having 6 carbon atoms or a tolyl group having 7 carbon atoms, and Ar₃ and Ar₄ are the same as or different from each other and are each independently selected from the group consisting of hydrogen; deuterium; tritium; an alkenyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; an aryl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a hetero ring group comprising O, N or S as a heteroatom, which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a carbazolyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; a fluorenyl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group; and nitrile group.

2. The compound according to claim 1, wherein $Ar_1$ in Formula 1 is selected from the group consisting of an aryl group which is unsubstituted or substituted by one or more substituent groups selected from the group consisting of a halogen group, an alkyl group, an alkoxy group, a substituted or unsubstituted aryl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; and a hetero ring group comprising O, N or S as a heteroatom, which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group, when $Ar_1$ is an aryl group, the aryl group is selected from the group consisting of a biphenyl group, terphenyl group, a naphthyl group, an anthracenyl group, a phenanthrene group, a pyrenyl group, a perylenyl group and a chrysenyl group, $Ar_2$ in Formula 1 is selected from the group consisting of an aryl group which is unsubstituted or substituted by one or more substituent groups selected from the group consisting of a halogen group, an alkyl group, an alkoxy group, a substituted or unsubstituted aryl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; and a hetero ring group comprising O, N or S as a heteroatom, which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group, and when $Ar_2$ is an aryl group, the aryl group is selected from the group consisting of a phenyl group, a biphenyl group, terphenyl group, a naphthyl group, an anthracenyl group, a phenanthrene group, a pyrenyl group, a perylenyl group and a chrysenyl group.

3. The compound according to claim 1, wherein L in Formula 1 is a direct bond; or an arylene group having 6 to 40 carbon atoms, which is unsubstituted or substituted by one or more substituent groups selected from the group consisting of nitro, nitrile, halogen, an alkyl group, and an alkoxy group.

4. The compound according to claim 1, wherein $Ar_3$ and $Ar_4$ in Formula 1 are the same as or different from each other and are each independently selected from the group consisting of hydrogen; deuterium; an aryl group which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; and a hetero ring group comprising O, N or S as a heteroatom, which is unsubstituted or substituted by one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group, and an acetylene group.

5. The compound according to claim 1, wherein Formula 1 is represented by the following Formula 2 or 3:

[Formula 2]

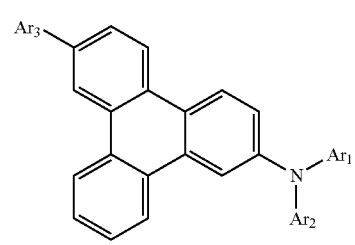

[Formula 3]

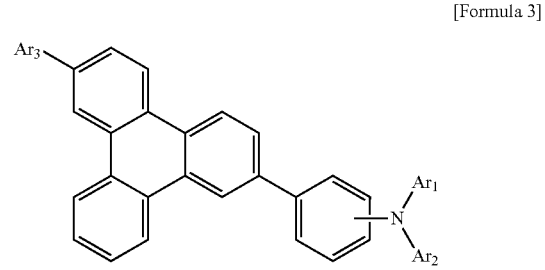

wherein $Ar_1$ to $Ar_3$ are the same as those defined in Formula 1.

6. The compound according to claim 1, wherein the compound is one selected from the group consisting of the following formulas:
[Formula 1-1]
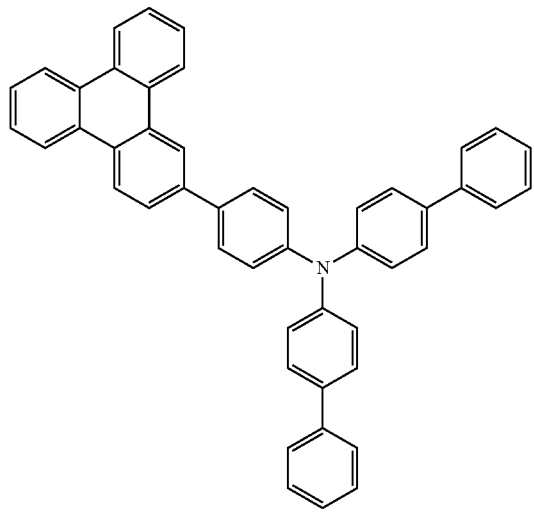
[Formula 1-2]
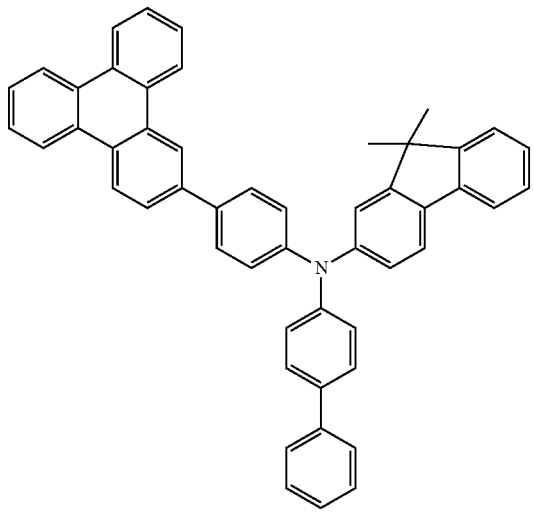
[Formula 1-3]
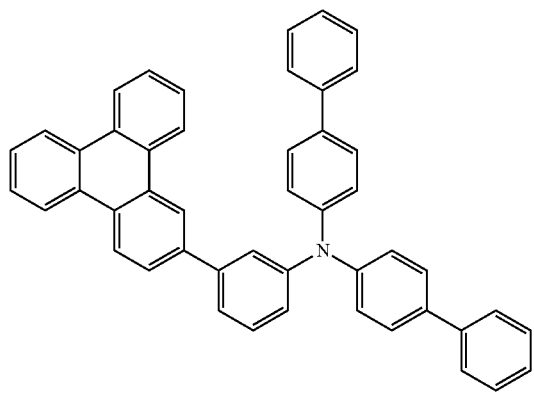
[Formula 1-4]
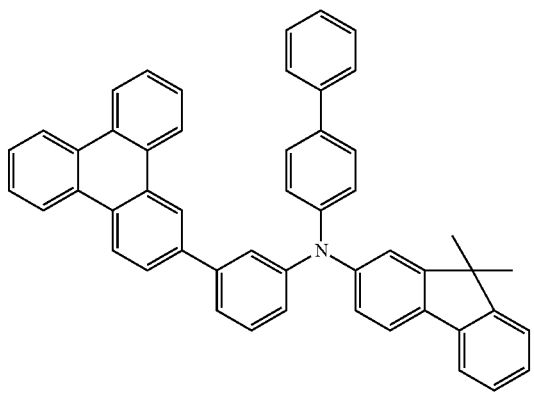
[Formula 1-5]
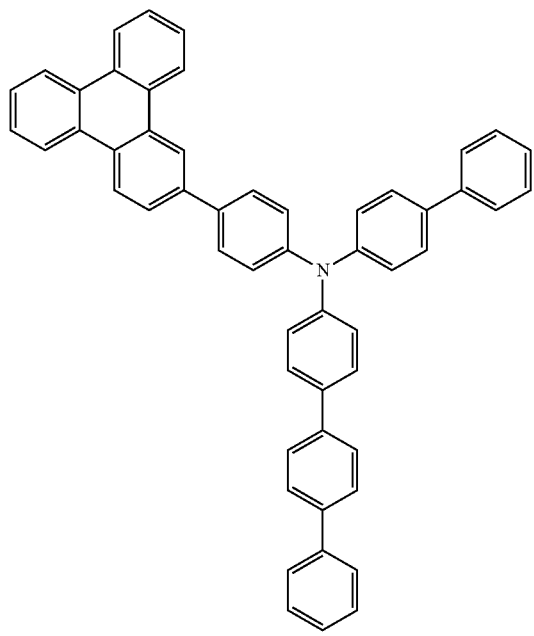
[Formula 1-6]
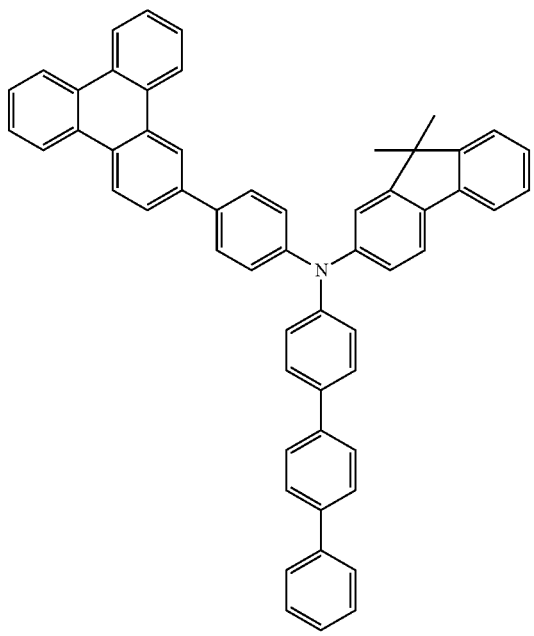

[Formula 1-7]
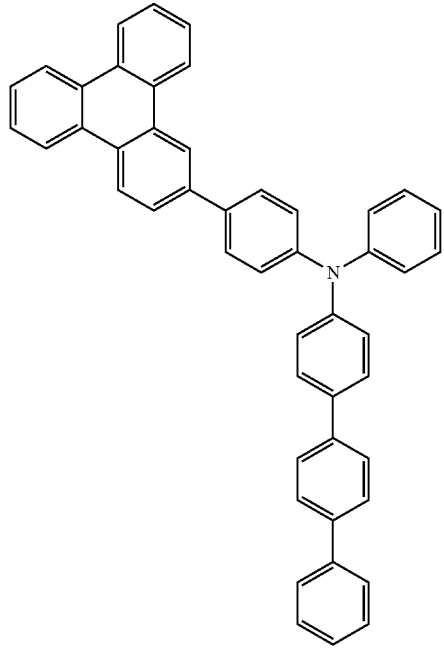
[Formula 1-8]
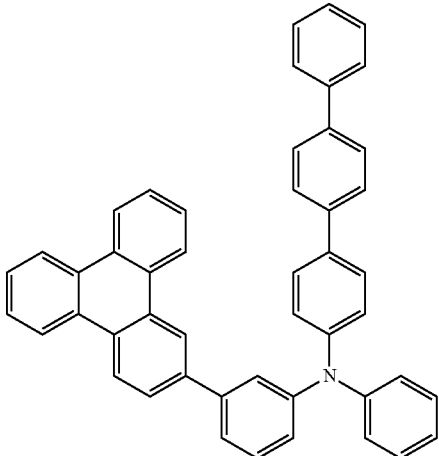
[Formula 1-9]
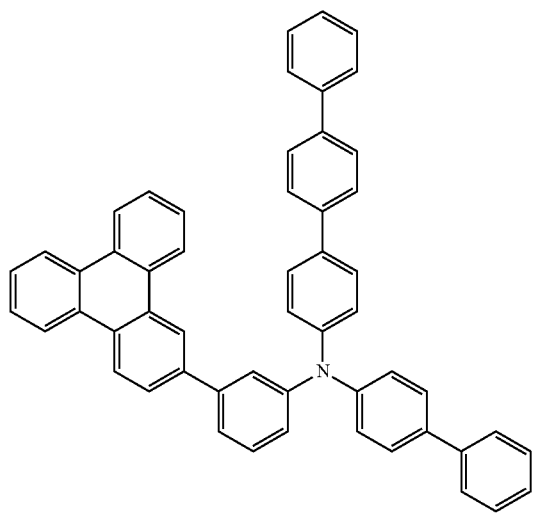
[Formula 1-10]
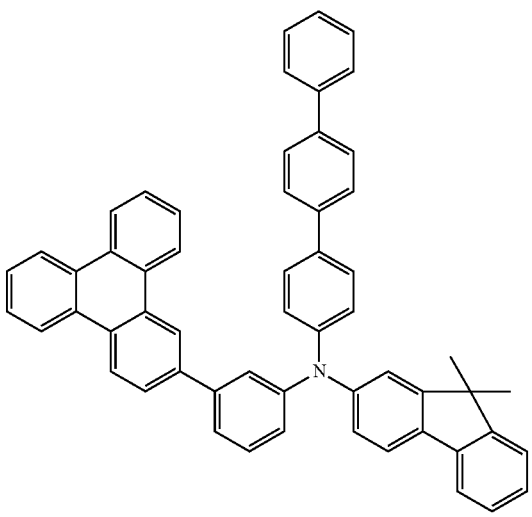
[Formula 1-11]
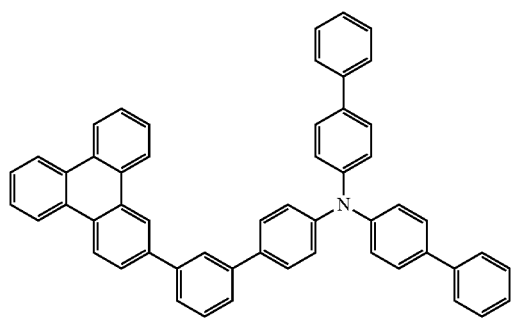
[Formula 1-12]
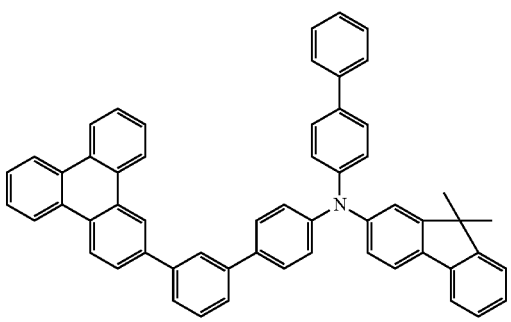

-continued
[Formula 1-13]
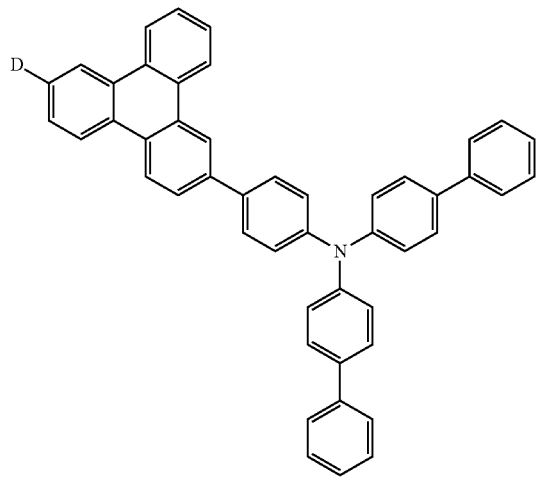
[Formula 1-14]
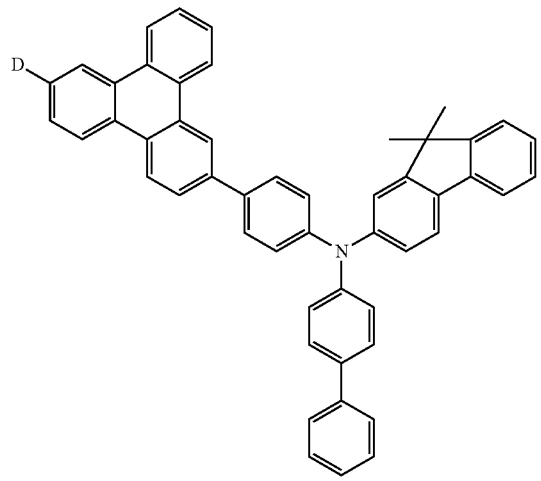
[Formula 1-15]
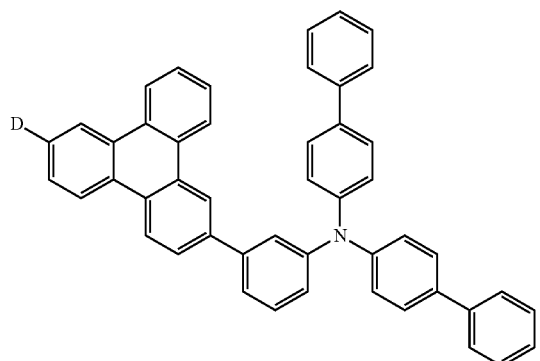
[Formula 1-16]
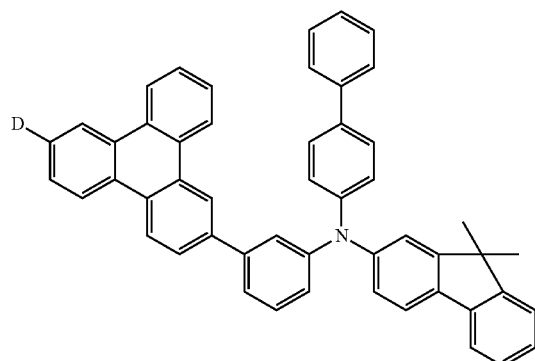
[Formula 1-17]
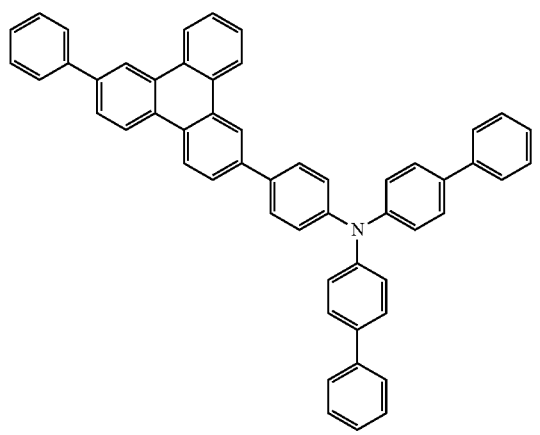
[Formula 1-18]
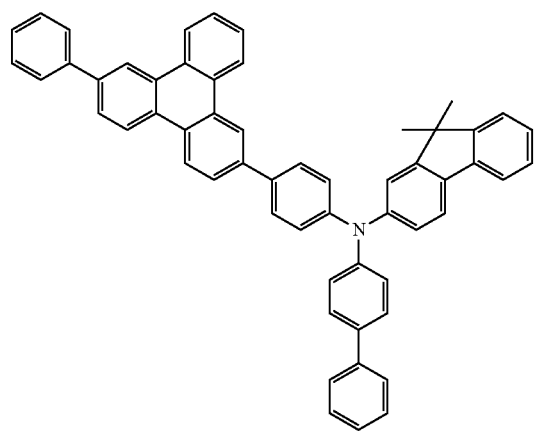

[Formula 1-19]
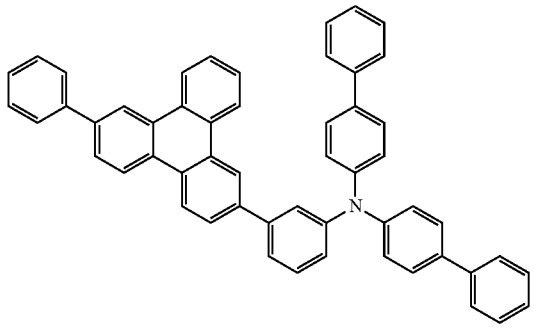
[Formula 1-20]
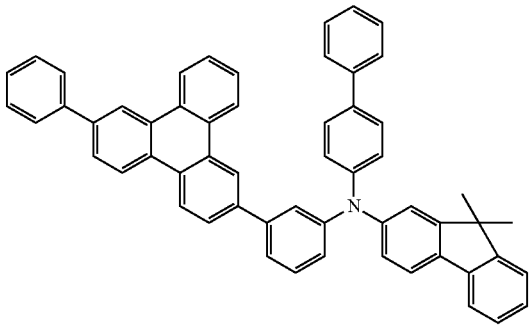
[Formula 1-21]
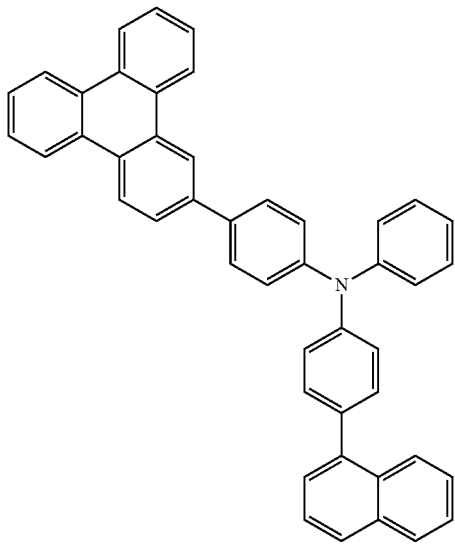
[Formula 1-22]
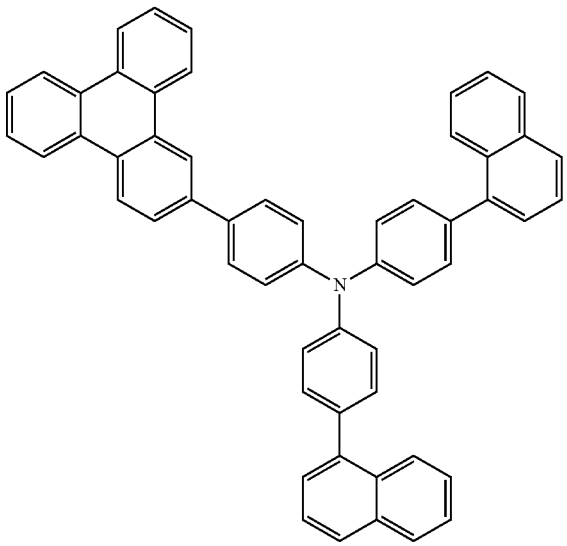
[Formula 1-23]
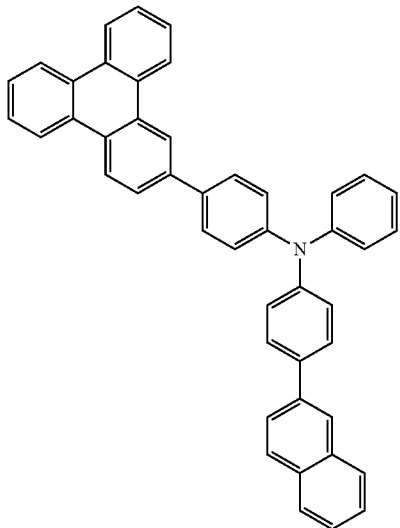
[Formula 1-24]
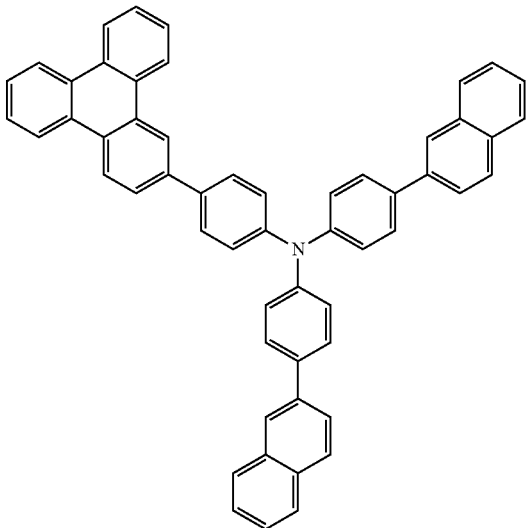

-continued
[Formula 1-25]
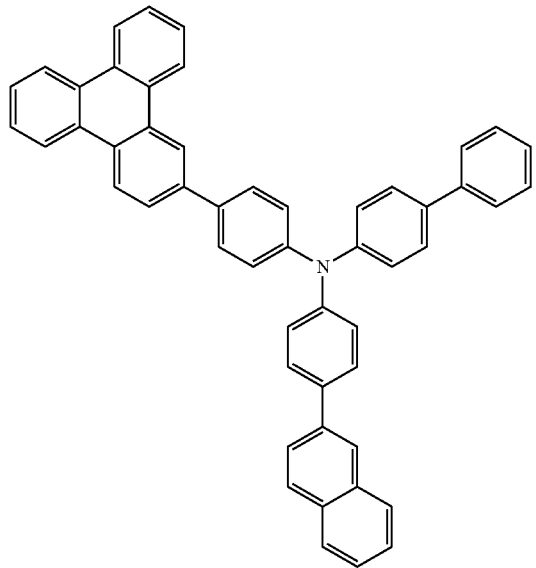
[Formula 1-26]
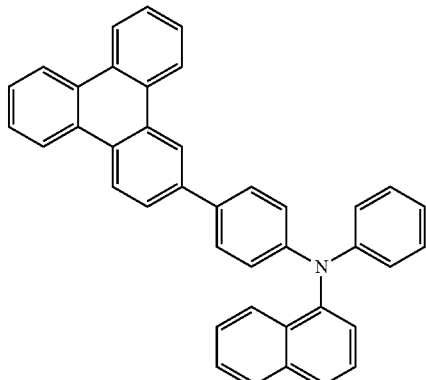
[Formula 1-27]
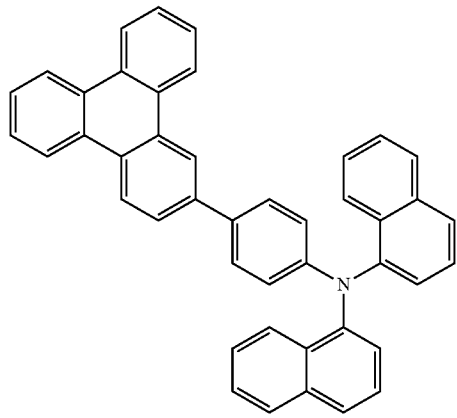
[Formula 1-28]
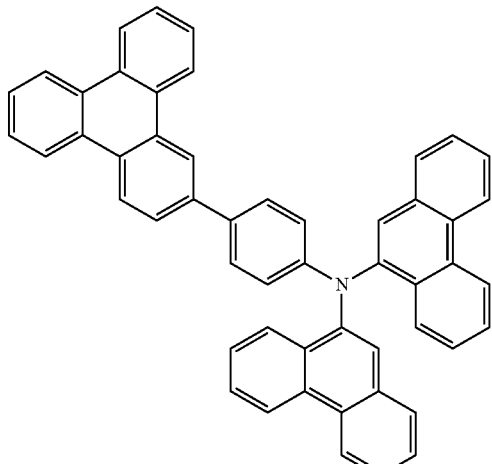
[Formula 1-29]
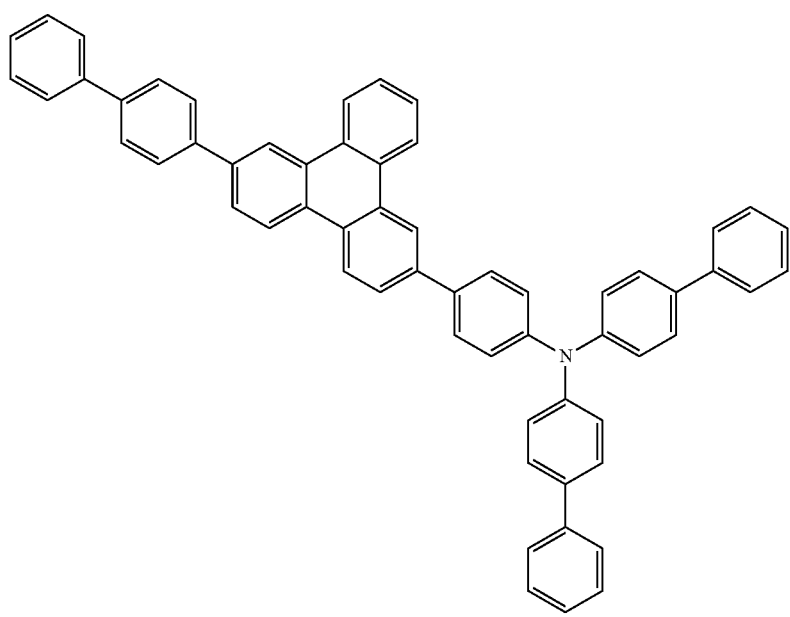

[Formula 1-30]
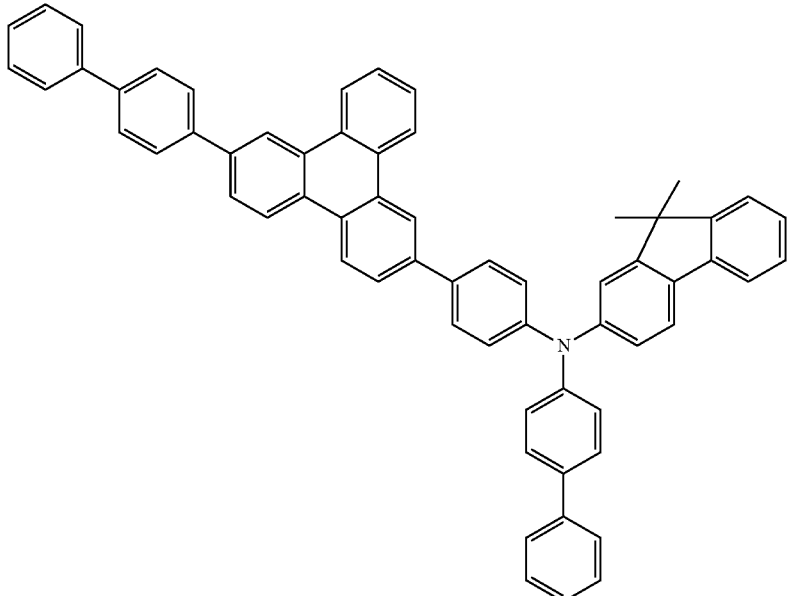
[Formula 1-31]
[Formula 1-32]
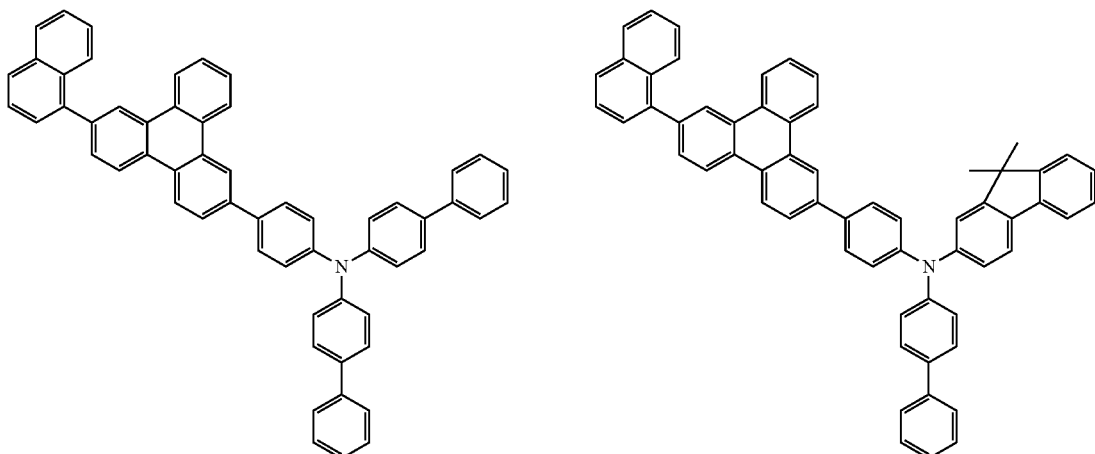
[Formula 1-33]
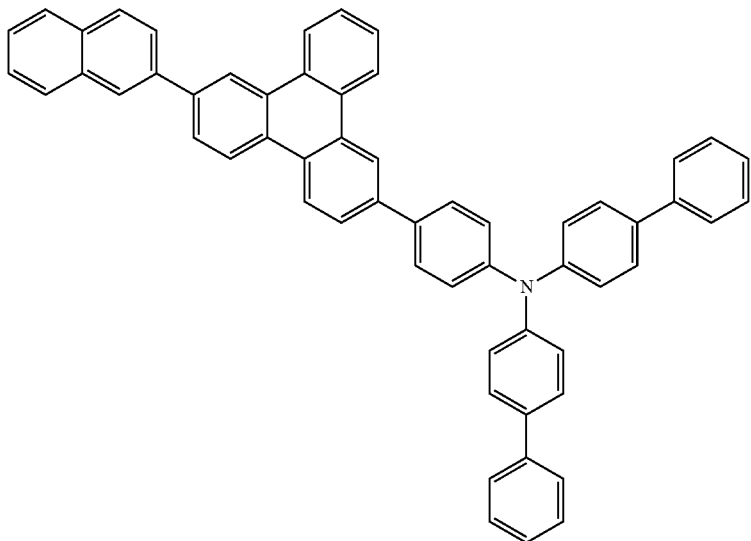

[Formula 1-34]
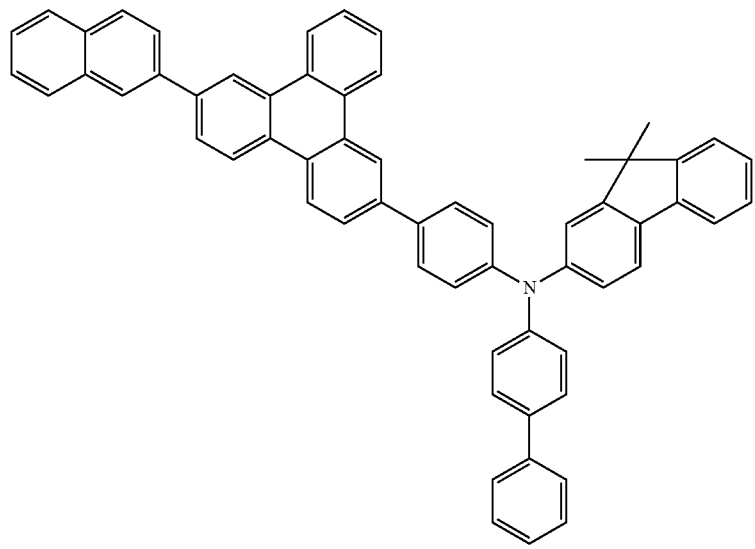
[Formula 1-35]
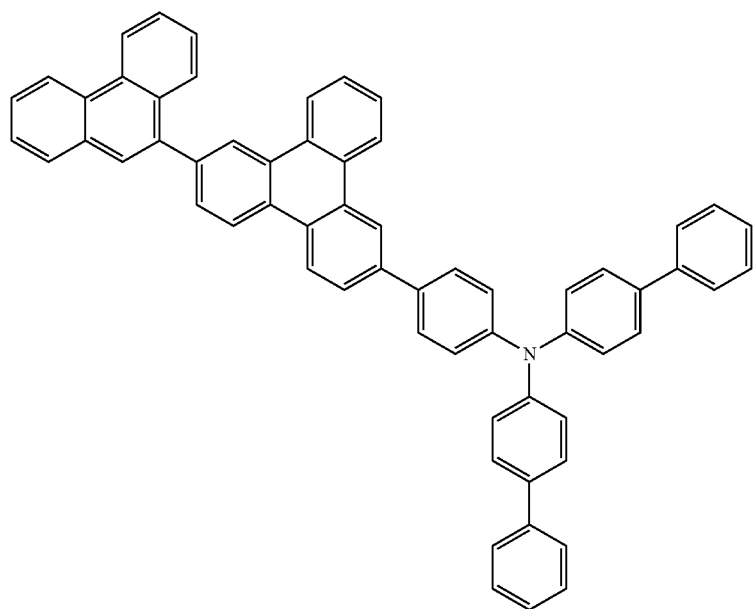

[Formula 1-36]
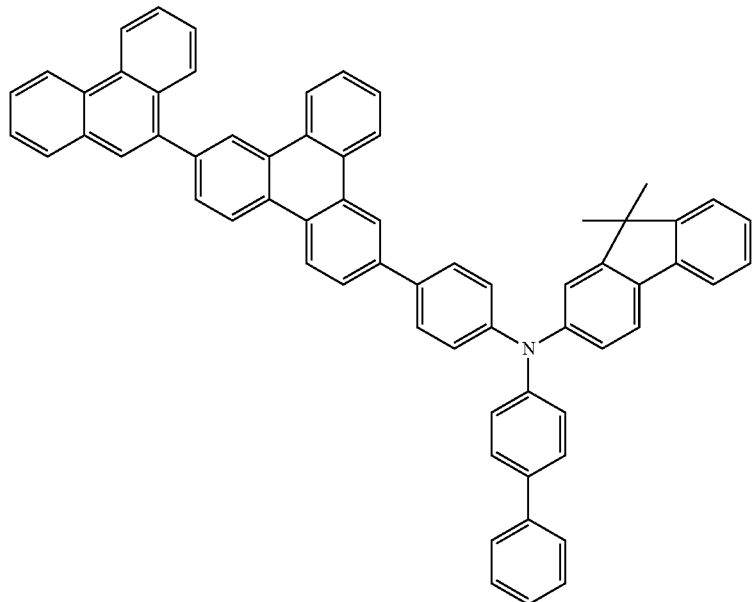
[Formula 1-37]
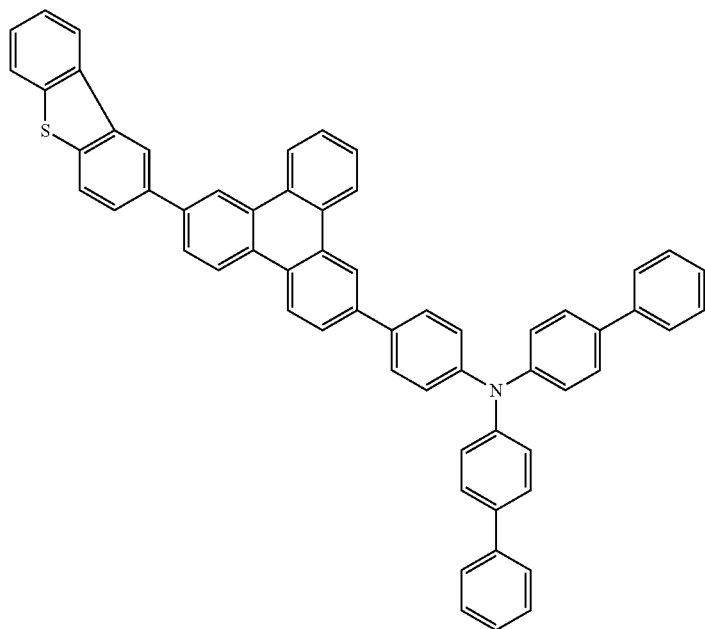

[Formula 1-38]
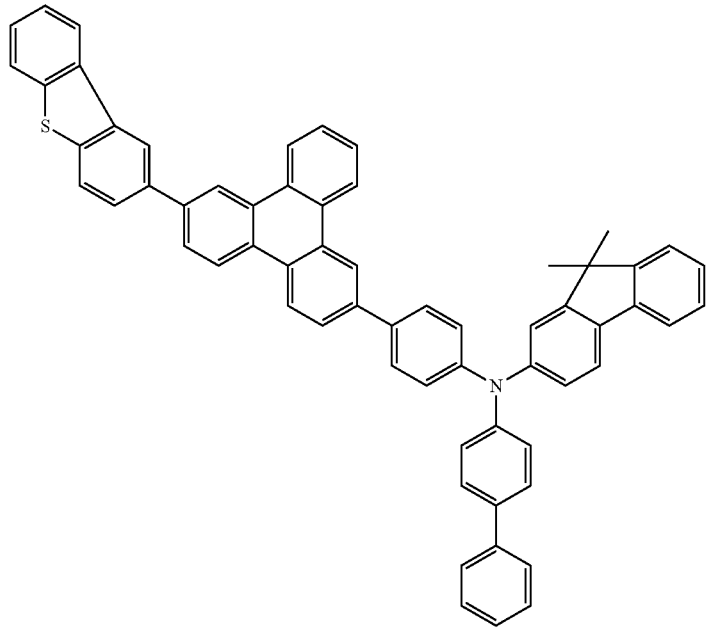
[Formula 1-39]
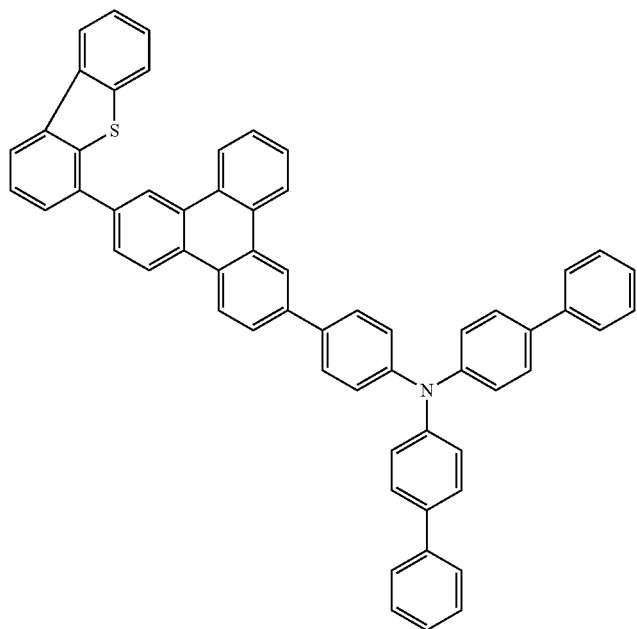

[Formula 1-40]
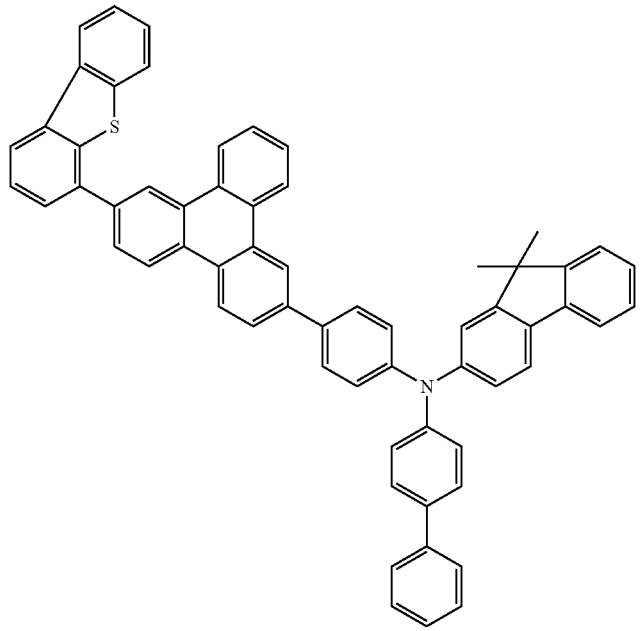
[Formula 1-41]
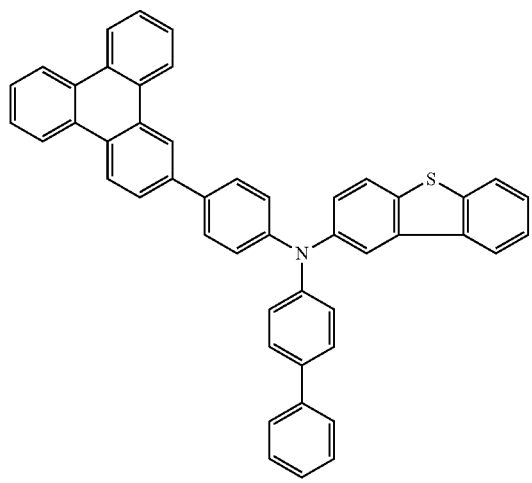
[Formula 1-42]
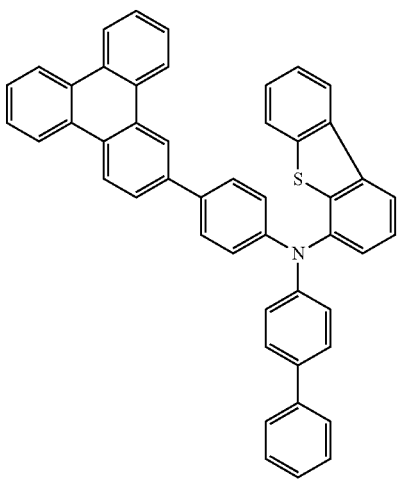
[Formula 1-43]
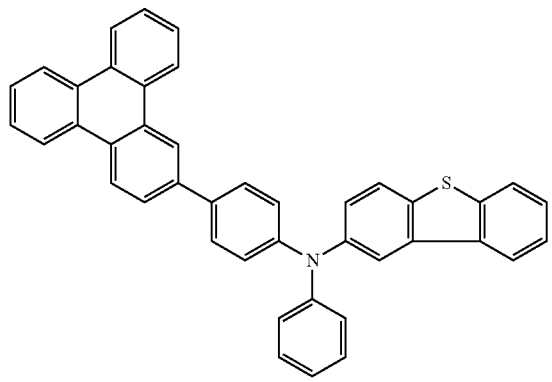
[Formula 1-44]
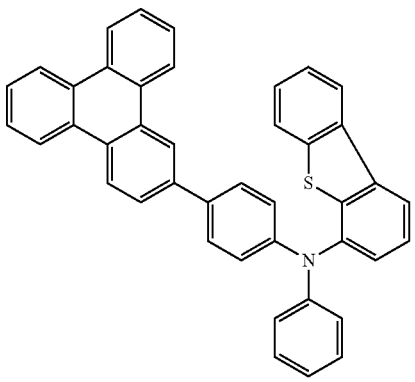

[Formula 1-45]
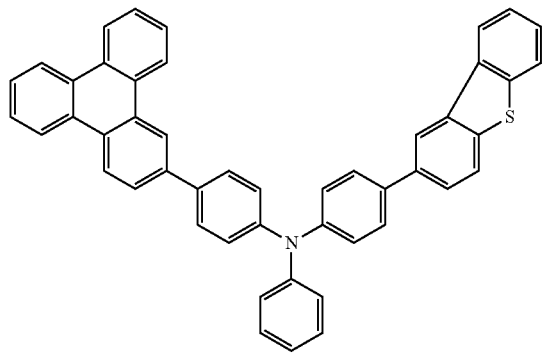
[Formula 1-46]
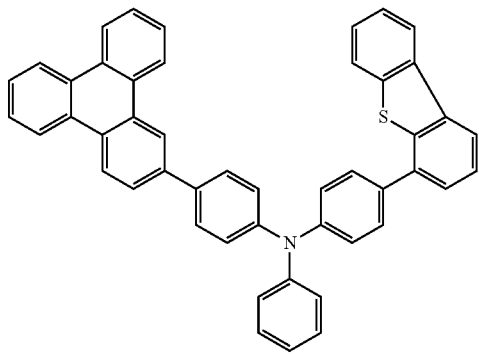
[Formula 1-47]
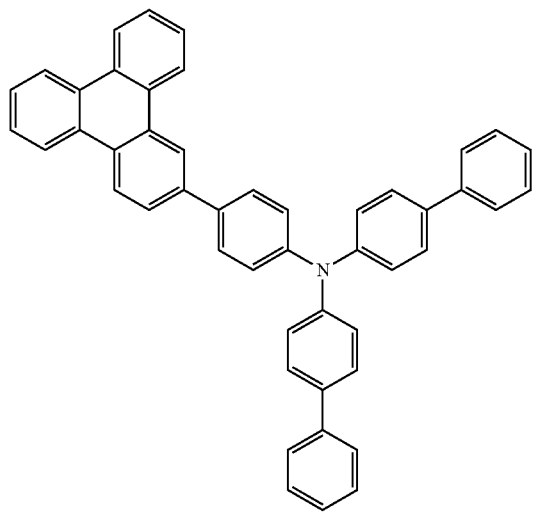
[Formula 1-48]
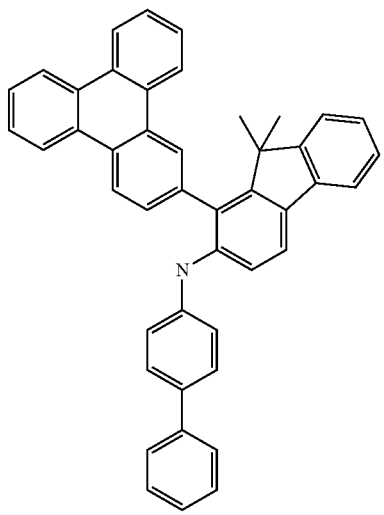
[Formula 1-49]
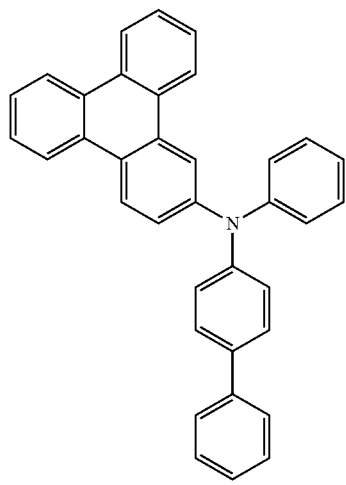
[Formula 1-50]
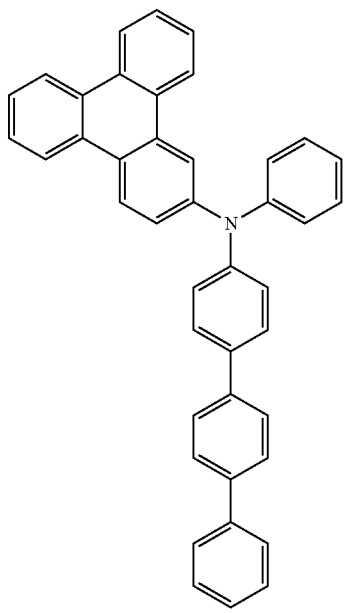

-continued

[Formula 1-51]

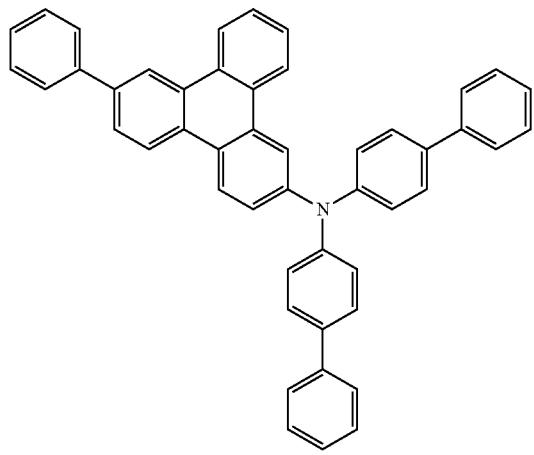

[Formula 1-52]

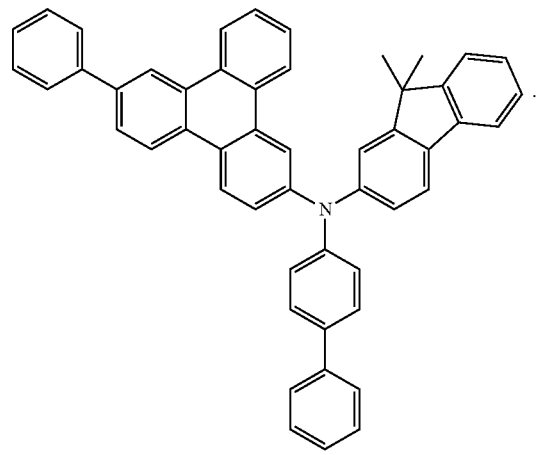

7. An organic light emitting device, comprising:
a first electrode;
a second electrode; and
an organic material layer having one or more layers disposed between the first electrode and the second electrode,
wherein one or more layers of the organic material layer comprises a compound of claim 1.

8. The organic light emitting device according to claim 7, wherein the organic material layer comprises a hole transporting layer, wherein the hole transporting layer comprises the compound represented by Formula 1.

9. The organic light emitting device according to claim 7, wherein the organic material layer comprises a hole injection layer, wherein the hole injection layer comprises the compound represented by Formula 1.

10. The organic light emitting device according to claim 7, wherein the organic material layer comprises a layer comprising hole injection and hole transportation simultaneously, wherein the layer comprises the compound represented by Formula 1.

11. The organic light emitting device according to claim 7, wherein the organic material layer comprises an electron injection layer and an electron transporting layer, wherein the electron injection layer and the electron transporting layer comprise the compound represented by Formula 1.

12. The organic light emitting device according to claim 7, wherein the organic material layer comprises a light emitting layer, wherein the light emitting layer comprises the compound represented by Formula 1.

* * * * *